United States Patent [19]
Acton

[11] Patent Number: 5,965,790
[45] Date of Patent: Oct. 12, 1999

[54] SR-BI REGULATORY SEQUENCES AND THERAPEUTIC METHODS OF USE

[75] Inventor: Susan Laurene Acton, Lexington, Mass.

[73] Assignee: Millennium Pharmaceuticals, Inc., Cambridge, Mass.

[21] Appl. No.: 08/812,204

[22] Filed: Mar. 6, 1997

[51] Int. Cl.[6] .............................. C12N 5/00; C12N 15/00; C07H 21/04

[52] U.S. Cl. ................................. 800/18; 800/21; 435/6; 435/29; 435/320.1; 435/325; 536/24.1; 536/24.31; 935/6; 935/36

[58] Field of Search .................................. 800/2, DIG. 1; 536/23.5, 24.1, 24.31; 514/44; 435/325, 320.1, 6, 29; 424/9.2; 935/6.36

[56] References Cited

U.S. PATENT DOCUMENTS 5,354,557  10/1994  Oppermann et al. .................... 424/423

FOREIGN PATENT DOCUMENTS 9416057  7/1994  WIPO .
WO 96/00288  1/1996  WIPO .

OTHER PUBLICATIONS

Acton, S.L. et al. "Expression Cloning of SR–BI, a CD36–related Class B Scavenger Receptor" *J. Biol. Chem.* 269(33):21003–21009, 1994.

Acton, S. et al. "Identification of Scavenger Receptor SR–BI as a High Density Lipoprotein Receptor" *Science* 271:518–520, 1996.

Calvo, D. and Vega, M.A. "Identification, primary structure, and distribution of CLA–1, a novel member of the CD36/ LIMPH gene family" *J. Biol. Chem.* 268(25):18929–18935, 1993.

Calvo, D. et al. "The CD36, CLA–1 (CD36L1), and LIMPII (CD36L2) Gene Family: Cellular Distribution, Chromosomal Location, and Genetic Evolution" *Genomics* 25:10–106, 1995.

Fukasawa, M. et al. "SRB1, a Class B scavenger receptor, recognizes both negatively charged liposomes and apoptotic cells" *Exper. Cell Research* 222:246–250, 1996.

Rigotti, A. et al. "The Class B Scavenger Receptors SR–BI and CD36 are Receptor for Anionic Phospholipids" *J. Biol. Chem.* 270 (27):16221–16224, 1995.

Tang, Y. et al. "Identification of a Human CD36 Isoform Produced by Exon Skipping" *J. Biol. Chem* 269 (8):6011–6015, 1994.

Wang, N. et al. "Scavenger Receptor BI (SR–BI) is up–regaulated in adrenal gland in apolipoprotein A–I and hepatic lipase knock–out mice as a response to depletion of cholesterol stores" *J. Biol. Chem* 271 (35):21001–21004, 1996.

*Primary Examiner*—Bruce R. Campell
*Attorney, Agent, or Firm*—Foley, Hoag & Eliot LLP

[57] ABSTRACT

The invention features nucleic acid molecules that are involved with (e.g. activate or regulate) human SR-BI receptor transcription, as well as complements thereto, and homologs thereof. In addition, drug discovery assays are provided for identifying agents which modulate SR-BI promoter activity and thereby modulate the expression of a gene regulated thereby. Such agents can be useful therapeutically for treating or preventing the development of a disease or condition that is caused or contributed to by an aberrant SR-BI activity. In a preferred embodiment, the disease or condition is characterized by inappropriate lipid transfer or metabolism (e.g., atherosclerosis or gallstone formation). Such agents can also be used to modulate expression of a specific gene under the control of the SR-BI promoter in gene therapy. Moreover, the present invention provides diagnostic assays and reagents for determining whether a subject has a disorder involving, for example, aberrant expression of SR-BI genes.

31 Claims, 3 Drawing Sheets

```
   1 GATCCTTCTGCCTCAGCCTCCTGAGTAGCTGGGGCCACAAGCGCATGCCA
  51 CTGTGGCTGGTTAATCTTTTCATTTTCTGTAGAGACTGGTCTCACTATGT
 101 TGCCCAGGCTGGTCTCCAACTAGTGGCCTCAAGTGATCCCTCACCTGGAC
 151 CTTCCAAAGTGCTGGGATTACAGTTGTGGGCCACCATGCACCGGGCCTGT
 201 TCTGTTTTCTTGGAGCACTTGCCTGCAATTATCCTTCATTCATTTGCTCA
 251 CGTGCTCATCATTGGTTTCCCTCTTCATTAGAAAGTGGGGACTTGGTTTG
 301 GGTTAACTAAGCTTCCCTGTGCATCAGTTTTCATTTCTTTCTTTCTTTTT
 351 CTTTTTCTTTTCTTTTTTTTTTTTTTTGAGATGGAGTTTCGCTCTTGTTG
 401 CCCAGGCTGGAGTGCAATGGCGCTATCTCGGCTCGCCACAACCTCCGCCT
 451 CCCGGGTTCAAGCGATTCTCCTGCCTCAGCCTCCTGAGTAGCTGAGATTA
 501 CAGGCATGCGCCACTACGCCTGGTTAATTTTGTATTGTTAGTAGAGACGG
 551 GGTTTCGCCATGTTGGTCAGGCTGGTCTCCAACTCCCGACCTCAGGTGAT
 601 CCATGAAGTCCACCCGCCTCGGCCTCCCAAAGTGCTGGGATTACAGGCGT
 651 GAGCCACCTCCCAGTTTTCTTATTGTAAAATGGAGCCATTGTGTGCAAAG
 701 CACTCAGGACAGGGGCCAGCACCTAGAAGGCTCCTCAGTCATTCATTCTA
 751 GAATATTTACTGTGAGCAGGCATTCCCTGCCAGGCCACGTTCTAGAGCTC
 801 AGGACGCGTGGGGGGGGGCCCGCCTCACGGGTTGGCATCCCAGTTGGAG
 851 CACATGGTCAGAATGCAAGGACGCAAATGAACGTGAACCTGCCAGGGGGT
 901 GCTCAGTCATAGGGTGATGGTGGCACCAGCGTTACGAAGGATAGGGCCAG
 951 GCGGATACCTGGGAGAACAGAATTGCCTGTGCAGGGTGTATGGAGGCCCT
1001 GGGGCTGGAGCCTGCGGGCTTCTTCCAGGGACAGTGAGGCTGGAGATGG
1051 ACTGCGGAGATGAGGGTCTAGAAGGTGGTGGCGGGGCATGTGGACCGTTG
1101 TAAGGGCTCTGGGGTTCCTGGGTGGGCTGGCGAAGTCCTACTCACAGTGA
1151 CCAACCATGATGATGGTCCCGATAGAGGAGGAGAGGGAGGAGGAGGGAAA
1201 AGGAAGGGTGAGGGCTCAGAGGGGAGAGCTGGGAGGAGGGAGACATAG
1251 GTGGGGGAAGGGGTAGGAGAAAGGGGAAGGGAGCAAGAGGGTGAGGGGCA
1301 CCAGGCCCCATAGACGTTTTGGCTCAGCGGCCACGAGGCTTCATCAGCTC
1351 CCGCCCCAAAACGGAAGCGAGGCCGTGGGGGCAGCGGCAGCATGGCGGGG
1401 CTTGTCTTGGCGGCCATGGCCCCGCCCCTGCCCGTCCGATCAGCGCCCC
1451 GCCCCGTCCCCGCCCCGACCCCGCCCCGGGCCCGCTCAGGCCCCGCCCCT
1501 GCCGCCGGAATCCTGAAGCCCAAGGCTGCCCGGGGCGGTCCGGCGGCGC
1551 CGGCGATGGGGCATAAAACCACTGGCCACCTGCCGGGCTGCTCCTGCGTG
1601 CGCTGCCGTCCCG
```

Promoter Region (at position ~1545)
TATA BOX (ATAAAA, positions ~1566-1571)
mRNA cap site (T at position ~1595)

FIG. 1

SEQUENCE LISTING (1) GENERAL INFORMATION:

(iii) NUMBER OF SEQUENCES: 8

(2) INFORMATION FOR SEQ ID NO:1:

(i) SEQUENCE CHARACTERISTICS:
      (A) LENGTH: 1613 base pairs
      (B) TYPE: nucleic acid
      (C) STRANDEDNESS: single
      (D) TOPOLOGY: linear (ii) MOLECULE TYPE: DNA (genomic)

(xi) SEQUENCE DESCRIPTION: SEQ ID NO:1:

```
GATCCTTCTG CCTCAGCCTC CTGAGTAGCT GGGGCCACAA GCGCATGCCA CTGTGGCTGG       60

TTAATCTTTT CATTTCTGT AGAGACTGGT CTCACTATGT TGCCCAGGCT GGTCTCCAAC       120

TAGTGGCCTC AAGTGATCCC TCACCTGGAC CTTCCAAAGT GCTGGGATTA CAGTTGTGGG      180

CCACCATGCA CCGGGCCTGT TCTGTTTTCT TGGAGCACTT GCCTGCAATT ATCCTTCATT      240

CATTTGCTCA CGTGCTCATC ATTGGTTTCC CTCTTCATTA GAAAGTGGGG ACTTGGTTTG      300

GGTTAACTAA GCTTCCCTGT GCATCAGTTT TCATTTCTTT CTTTCTTTTT CTTTTTCTTT      360

TCTTTTTTTT TTTTTTTGAG ATGGAGTTTC GCTCTTGTTG CCCAGGCTGG AGTGCAATGG      420

CGCTATCTCG GCTCGCCACA ACCTCCGCCT CCCGGGTTCA AGCGATTCTC CTGCCTCAGC      480

CTCCTGAGTA GCTGAGATTA CAGGCATGCG CCACTACGCC TGGTTAATTT TGTATTGTTA      540
```

```
GTAGAGACGG GGTTTCGCCA TGTTGGTCAG GCTGGTCTCC AACTCCCGAC CTCAGGTGAT      600

CCATGAAGTC CACCCGCCTC GGCCTCCCAA AGTGCTGGGA TTACAGGCGT GAGCCACCTC      660

CCAGTTTTCT TATTGTAAAA TGGAGCCATT GTGTGCAAAG CACTCAGGAC AGGGGCCAGC      720

ACCTAGAAGG CTCCTCAGTC ATTCATTCTA GAATATTTAC TGTGAGCAGG CATTCCCTGC      780

CAGGCCACGT TCTAGAGCTC AGGACGCGTG GGGGGGGGGC CCGCCTCACG GGTTGGCATC      840

CCAGTTGGAG CACATGGTCA GAATGCAAGG ACGCAAATGA ACGTGAACCT GCCAGGGGGT      900

GCTCAGTCAT AGGGTGATGG TGGCACCAGC GTTACGAAGG ATAGGGCCAG GCGGATACCT      960

GGGAGAACAG AATTGCCTGT GCAGGGTGTA TGGAGGCCCT GGGGCTGGAG CCTGCGGGGC     1020

TTCTTCCAGG GACAGTGAGG CTGGAGATGG ACTGCGGAGA TGAGGGTCTA GAAGGTGGTG     1080

GCGGGGCATG TGGACCGTTG TAAGGGCTCT GGGGTTCCTG GGTGGGCTGG CGAAGTCCTA     1140

CTCACAGTGA CCAACCATGA TGATGGTCCC GATAGAGGAG GAGAGGGAGG AGGAGGGAAA     1200

AGGAAGGGTG AGGGGCTCAG AGGGGAGAGC TGGGAGGAGG GGAGACATAG GTGGGGGAAG     1260

GGGTAGGAGA AAGGGGAAGG GAGCAAGAGG GTGAGGGGCA CCAGGCCCCA TAGACGTTTT     1320

GGCTCAGCGG CCACGAGGCT TCATCAGCTC CCGCCCCAAA ACGGAAGCGA GGCCGTGGGG     1380

GCAGCGGCAG CATGGCGGGG CTTGTCTTGG CGGCCATGGC CCCGCCCCCT GCCCGTCCGA     1440

TCAGCGCCCC GCCCCGTCCC CGCCCCGACC CCGCCCCGGG CCCGCTCAGG CCCCGCCCCT     1500

GCCGCCGGAA TCCTGAAGCC CAAGGCTGCC CGGGGGCGGT CCGGCGGCGC CGGCGATGGG     1560

GCATAAAACC ACTGGCCACC TGCCGGGCTG CTCCTGCGTG CGCTGCCGTC CCG           1613

(2) INFORMATION FOR SEQ ID NO:2:

(i) SEQUENCE CHARACTERISTICS:
        (A) LENGTH: 62 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:2:

GGGCGGTCCG GCGGCGCCGG CGATGGGGCA TAAAACCACT GGCCACCTGC CGGGCTGCTC       60

CT                                                                     62

(2) INFORMATION FOR SEQ ID NO:3:

(i) SEQUENCE CHARACTERISTICS:
        (A) LENGTH: 100 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:3:

CCGCCCCTGC CGCCGGAATC CTGAAGCCCA AGGCTGCCCG GGGCGGTCC GGCGGCGCCG        60

GCGATGGGGC ATAAAACCAC TGGCCACCTG CCGGGCTGCT                            100

(2) INFORMATION FOR SEQ ID NO:4:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: other nucleic acid
```

-continued (A) DESCRIPTION: /desc = "oligonucleotide"

(xi) SEQUENCE DESCRIPTION: SEQ ID NO:4:

GCCAGTGGTT TTATGCCCCA                                              20

(2) INFORMATION FOR SEQ ID NO:5:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "oligonucleotide"

(xi) SEQUENCE DESCRIPTION: SEQ ID NO:5:

GGAGCAGCCC GGCAGGTG                                                18

(2) INFORMATION FOR SEQ ID NO:6:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "oligonucleotide"

(xi) SEQUENCE DESCRIPTION: SEQ ID NO:6:

CGCCGGGCCG CCCCCGGGCA                                              20

(2) INFORMATION FOR SEQ ID NO:7:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "oligonucleotide"

(xi) SEQUENCE DESCRIPTION: SEQ ID NO:7:

AGCGGGCCCG GGGCGGGGTC                                              20

(2) INFORMATION FOR SEQ ID NO:8:

(i) SEQUENCE CHARACTERISTICS:
        (A) LENGTH: 15 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "primer"

(xi) SEQUENCE DESCRIPTION: SEQ ID NO:8:

GGAGACGGGG ACGGC                                                   15

SR-BI REGULATORY SEQUENCES AND THERAPEUTIC METHODS OF USE

1. BACKGROUND OF THE INVENTION

Coronary heart disease is a major health risk throughout the industrialized world. Atherosclerosis, the most prevalent of cardiovascular diseases, is the principal cause of heart attack, stroke, and gangrene of the extremities, and thereby the principle cause of death in the United States. Although historically much emphasis has been placed on total plasma cholesterol levels as a risk factor for coronary heart disease, it has been clearly established that low levels of high density lipoprotein cholesterol (HDL-C) is an independent risk factor for this disease. Family and twin studies have shown that there are genetic components that affect HDL levels. However, mutations in the main protein components of HDL (ApoAI and ApoAII) and in the enzymes that are known to be involved in HDL metabolism (e.g., CETP, HL, LPL and LCAT) do not explain all of the genetic factors affecting HDL levels in the general population (J. L. Breslow, in *The Metabolic and Molecular Bases of Inherited Disease*, C. R. Scriver, A. L. Beaudet, W. Sly, D. Valle, Eds. (McGraw-Hill, New York, 1995), pp 2031–2052; and S. M. Grundy, (1995) *J. Am. Med. Assoc.* 256: 2849). This finding in combination with the fact that the mechanisms of HDL metabolism are poorly understood, suggests that there are other as yet unknown factors that contribute to the genetic variability of HDL levels.

Variations in the expression of the SR-BI receptor, which has been shown to bind HDL and LDL cholesterol and mediate uptake into cells (Acton, S. et al., (1996) *Science* 271:518–520) is likely to contribute to genetic lipoprotein variability, thereby playing a role in the development of atherosclerosis.

In addition, variations in the expression of the SR-BI receptor could be involved in cholesterol gallstone formation, since the SR-BI receptor is likely to be involved in transferring HDL-cholesterol from extrahepatic tissues to the liver (reverse cholesterol transport) e.g. for incorporation into bile (J. L. Breslow, in *The Metabolic and Molecular Bases of Inherited Disease*, C. R. Scriver, A. L. Beaudet, W. Sly, D. Valle, Eds. (McGraw-Hill, New York, 1995), pp 2031–2052; S. M. Grundy, (1995) *J. Am. Med. Assoc.* 256: 2849; G. Assman, A. von Eckardstein, H. B. Brewer Jr. in *The Metabolic and Molecular Bases of Inherited Disease*, C. R. Scriver, A. L. Beaudet, W. Sly, D. Valle, Eds. (McGraw-Hill, New York, 1995), pp 2053–2072; W. J. Johnson et al., (1991) *Biochem. Biophys. Acta* 1085:273; M. N. Pieters et al., (1994) *Ibid* 1225:125; and C. J. Fielding and P. E. Fielding, (1995) *J. Lipid Res* 36:211).

Further, variations in the expression of the SR-BI receptor could influence the fertility of a subject, since SR-BI appears to be involved in HDL-cholesteryl ester delivery to steroidogenic tissues (ovary, adrenal glands and testis) for hormone synthesis (Acton, S. et al., (1996) *Science* 271:518–520; Landschulz, et al., (1996) *J. Clin. Invest.* 98:984–95; J. M. Anderson and J. M. Dietschy (1981) *J. Biol. Chem.* 256: 7362; M. S. Brown et al., (1979) *Recent Prog Horm. Res.* 35:215; J. T. Gwynne and J. F. Strauss III, (1982) *Endocr. Rev.* 3:299; B. D. Murphy et al., (1985) *Endocrinology* 116: 1587).

Therapeutic agents for treating diseases which are caused or contributed to by inappropriate lipid (e.g. lipoprotein) transfer or metabolism (e.g. atherosclerosis or gallstone formation) are needed.

2. SUMMARY OF THE INVENTION

The present invention is based at least in part on the discovery of nucleic acid sequences that can activate or regulate transcription of SR-BI receptors (i.e. SR-BI transcriptional nucleic acids). In preferred embodiments, the nucleic acids comprise a basic SR-BI promoter or an SR-BI regulatory element (e.g. transcription factor binding site). Exemplary nucleic acids contained in plasmid bearing *E. coli* strains pSA-12 and pmd 21 have been deposited with the American Type Culture Collection (ATCC) on Jan. 24, 1997 (ATCC designation number 98304) and on Mar. 5, 1997 (ATCC designation number 97907). The SR-BI transcriptional nucleic acid in the plasmid contained in pSA-12 (sa-12) is approximately 1613 base pairs in length and the SR-BI transcriptional nucleic acid in the plasmid contained in pmd 21 is approximately 7 kb in length. The nucleic acid sa-12 comprises the nucleotide sequence shown in FIG. 1 (SEQ ID NO: 1). Based on expression studies in two distinct cell types, the sa-12 regulatory nucleic acid exhibits cell-specific properties (i.e., it is active in hepatocytes, but not in endothelial cells).

Accordingly, in one aspect, the invention features isolated SR-BI transcriptional nucleic acids and complements thereto. In one embodiment, the nucleic acid can hybridize to the transcriptional nucleic acids contained in ATCC designation numbers 98304 or 97907; or to the complement of the regulatory nucleic acids contained in ATCC designation numbers 98304 or 97907. In a preferred embodiment, the claimed nucleic acid can hybridize with at least a portion of the nucleic acid sequence provided as SEQ. ID. No: 1, 2, or 3; or to at least a portion of the complement of the nucleic acid sequence designated as SEQ. ID. Nos: 1, 2 or 3.

The invention also provides probes and primers comprising substantially purified oligonucleotides, which correspond to a region of nucleotide sequence which hybridizes to at least 6 consecutive nucleotides of the sequence set forth as SEQ ID Nos: 1, 2, or 3 or to the complement of the sequences set forth as SEQ ID Nos: 1, 2, or 3; or naturally occurring mutants thereof. In preferred embodiments, the probe/primer further includes a label group attached thereto, which is capable of being detected.

The invention further describes vectors comprised of the claimed nucleic acids; host cells transfected with said vectors whether prokaryotic or eukaryotic; and transgenic non-human animals which contain a heterologous form of a functional or non-functional SR-BI promoter as described herein. Such a transgenic animal can serve as an animal model for studying cellular and tissue disorders involving functional or non-functional SR-BI transcriptional nucleic acids or for use in drug screening or recombinant protein production.

In another aspect, the invention features pharmaceutical compositions comprised of molecules that modulate (agonize or antagonize) transcription from an SR-BI promoter, thereby activating, increasing or suppressing the expression level of a gene under the control of the SR-BI transcriptional nucleic acids. Particularly preferred molecules for use as pharmaceutical compositions are selected from the group consisting of: proteins, peptides, peptidomimetics, other small molecules (e.g. carbohydrates, lipids or small organic molecules) or nucleic acids (e.g. sense, antisense, ribozyme and triplex nucleic acid constructs).

In another aspect, the invention provides methods for treating a subject for a disease or condition, which is associated with (e.g., characterized, caused, or contributed to by) an aberrant SR-BI activity (e.g., insufficient or surplus functional SR-BI receptor or insufficient or surplus promoter activity), comprising administering to the subject an effective amount of a compound which is capable of modulating (agonizing or antagonizing) transcription from an SR-BI transcriptional nucleic acid, thereby activating, increasing or decreasing the expression level of a gene under the control of the SR-BI transcriptional nucleic acid. The compound can be an agonist of SR-BI transcriptional activity or an antagonist of SR-BI transcriptional activity. The compound can also be a compound that is capable of modulating an interaction between a basic promoter or a regulatory element and a transcription factor. Also within the scope of the invention is the use of compounds which are capable of modulating the activity of a transcription factor which itself modulates the activity of an SR-BI transcriptional nucleic acid.

Examples of diseases or conditions, which are associated with (e.g., characterized, caused, or contributed to by) an aberrant SR-BI activity include disorders that are caused by or contributed to by aberrant (e.g. insufficient or surplus) lipid (e.g. HDL or LDL) transport or metabolism in a subject (e.g. atherosclerosis, biliary tract disorders, such as gallstone formation and abnormal lipoprotein levels in a subject). Particularly preferred therapeutic molecules are selected from the group consisting of: proteins, peptides, peptidomimetics, other small molecules (e.g. carbohydrates, lipids or small organic molecules) or nucleic acids (e.g. sense, antisense, ribozyme and triplex nucleic acid constructs).

In yet another aspect, the invention provides assays for screening test compounds to identify molecules that modulate (agonize or antagonize) transcription from an SR-BI transcriptional nucleic acid, thereby activating, increasing or suppressing the expression level of a gene under the control of the transcriptional nucleic acid. In one embodiment, the assay is essentially comprised of the steps of: (i) combining a test compound with a functional reporter construct comprised of a gene encoding a reporter molecule (e.g., luciferase) under the control of at least a basic SR-BI promoter and optionally also at least one regulatory element; and (ii) detecting the level of expression of the reporter gene, wherein a statistically significant change in the level of expression (relative to expression in the absence of the test compound) indicates that the test compound modulates (agonizes or antagonizes) transcription from an SR-BI promoter.

In another embodiment, the assay is comprised of the steps of: (i) combining an SR-BI transcription factor with a test compound and a functional reporter construct comprised of a gene encoding a reporter molecule (e.g. luciferase) under the control of the SR-BI basic promoter and at least one regulatory element, which is a binding site for the transcription factor; and (ii) detecting the level of expression of the reporter gene, wherein a statistically significant change in the level of expression (relative to expression in the absence of test compound) is indicative of a modulation of SR-BI promoter mediated gene expression.

A further aspect of the present invention provides a method for determining whether a subject has or is at risk for developing a disorder which is associated with (e.g. characterized, caused or contributed to by) an aberrant SR-BI activity. In a preferred embodiment, the disease or condition is caused by or contributed by an inappropriate lipid (e.g. HDL or LDL) transfer or metabolism. For example, too low of a level of HDL or too high a level of LDL indicates an increased risk for developing atherosclerosis. In addition, too high a cholesterol level with respect to bile acids and lecithin in the gall bladder can predispose a subject to gallstone formation.

In general, diagnostic methods of the invention can include detecting, in a tissue of the subject, the presence or absence of a genetic lesion characterized by at least one of: a deletion of one or more nucleotides from an SR-BI promoter; an addition of one or more nucleotides to an SR-BI promoter, or a substitution of one or more nucleotides in an SR-BI promoter. For example, detecting the genetic lesion can include (i) providing a probe/primer comprised of an oligonucleotide which hybridizes to an SR-BI promoter or naturally occurring mutants; (ii) contacting the probe/primer with an appropriate nucleic acid containing sample; and (iii) detecting, by hybridization of the probe/primer to the nucleic acid, the presence or absence of the genetic lesion; e.g., wherein detecting the lesion comprises utilizing the probe/primer to determine the nucleotide sequence of the SR-BI promoter. For instance, the primer can be employed in a polymerase chain reaction (PCR) or in a ligation chain reaction (LCR).

Alternatively, the method can consist of determining the SR-BI receptor mRNA or protein level in a subject and comparing that level to the mRNA or protein level determined for a normal subject, wherein a lower level of SR-BI receptor mRNA or protein in the subject is indicative of a mutant SR-BI promoter. The method can also include detecting chromosomal abnormalities, such as chromosomal rearrangements in the SR-BI gene.

Other features and advantages of the invention will be apparent from the following detailed description and claims.

3. BRIEF DESCRIPTION OF THE FIGURES

FIG. 1 is a schematic depiction of the 1.6 kb sequence (sa-12), which is contained in the plasmid bearing *E. coli* strain pSA-12 (ATCC designation No.98304). The basic promoter region (indicated by arrows) including the TATA-like box (in box) and the mRNA cap site (underlined) as determined by use of the GRAIL computer program (http://avalon.emp.orn.gov/Grail-bin/Empty Grail) are indicated.

4. DETAILED DESCRIPTION OF THE INVENTION

4.1. General

Figure 2:
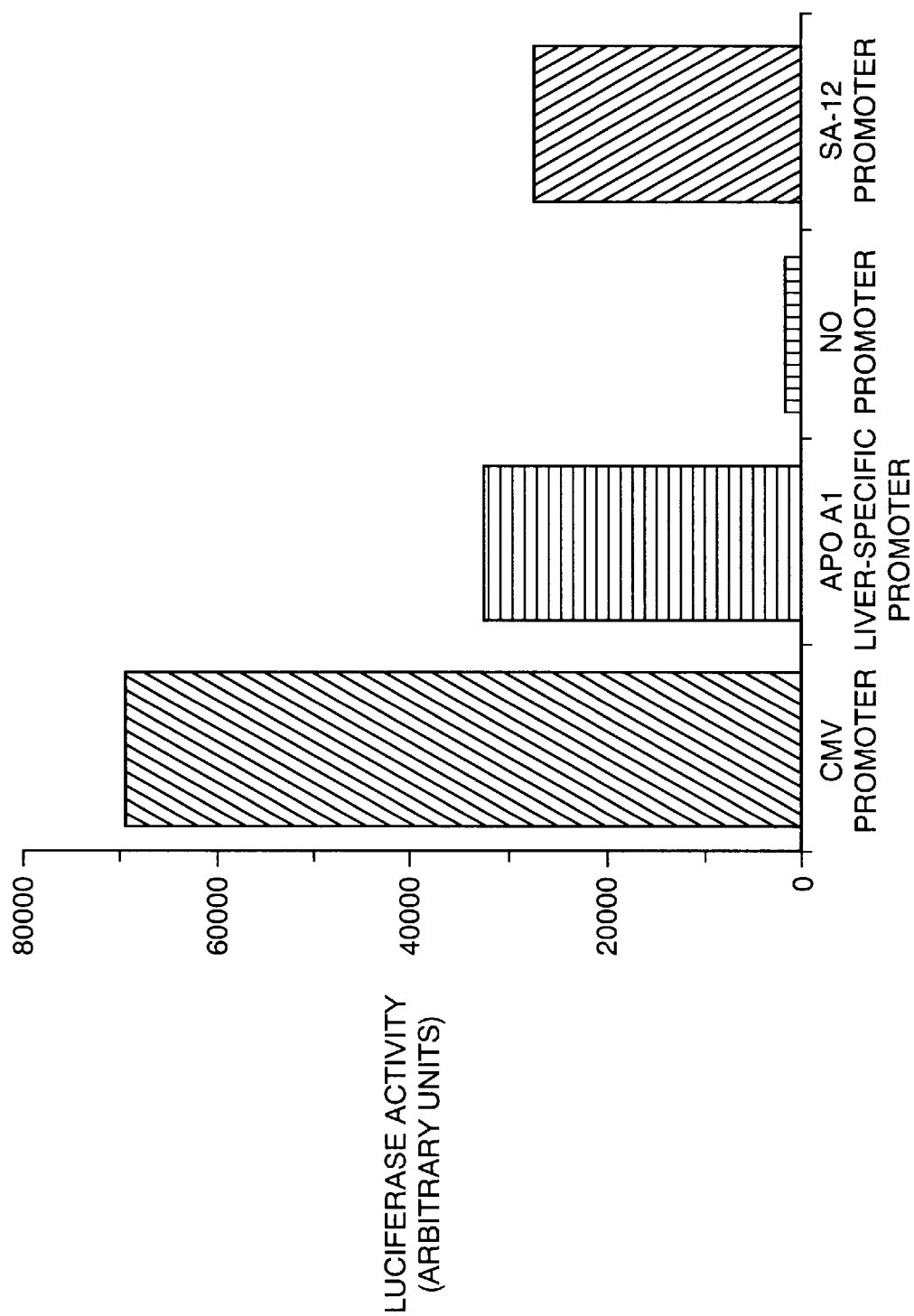
FIG. 2 is a bar graph plotting luciferase activity from hepatocellular carcinoma, HepG2 cells, which were transiently transfected with the pGL3-Basic promoterless vector alone or driven by: the cytomegalovirus (CMV) promoter, the ApoA1 liver specific promoter, or the SR-BI promoter (sa-12).

The present invention is based at least in part on the discovery of transcriptional nucleic acid sequences (e.g. basic promoter and regulatory elements) that regulate SR-BI receptor expression. Exemplary nucleic acids contained in plasmid bearing *E. coli* strains pSA-12 and pmd 21 have been deposited with the American Type Culture Collection (ATCC) on Jan. 24, 1997 (ATCC designation number 98304) and on Mar. 5, 1997 (ATCC designation number 97907). The SR-BI transcriptional nucleic acid in the plasmid contained in pSA-12 (sa-12) is approximately 1613 base pairs in length and the SR-BI transcriptional nucleic acid in the plasmid contained in pmd 21 is approximately 7 kb in length. The nucleic acid sa-12 comprises the nucleotide sequence shown in FIG. 1 (SEQ ID NO: 1). The basic promoter region as determined using the GRAIL computer program is comprised of nucleotides 1534–1595 (SEQ. ID. No. 2). Transcription initiation indicated as the mRNA cap site appears to occur at nucleotide 1595 as shown in FIG. 1. Nucleotides 1493–1592 of sa-12 (SEQ. ID. No. 3) were found to be negative in Northern experiments, confirming that this region is not transcribed, as is characteristic of a basic promoter region. Based on expression studies, the nucleic acid sa-12 is capable of regulating gene expression in a tissue specific manner (e.g., it functions in hepatocyte cell lines, but not endothelial cell lines). SR-BI mRNA, having a major transcript size of approximately 2.9 kb, has been found to be highly expressed in adrenals, ovaries, liver and placenta, indicating that the SR-BI promoter is functional in these cell types.

Accordingly, certain aspects of the present invention relate to nucleic acid molecules that are involved with (e.g. activate or regulate) human SR-BI receptor transcription, as well as complements thereto, and homologs thereof. In addition, drug discovery assays are provided for identifying agents which modulate SR-BI promoter activity and thereby modulate the expression of an SR-BI receptor. Such agents can be useful therapeutically for treating or preventing the development of a disease or condition that is caused or contributed to by an aberrant SR-BI activity. In a preferred embodiment, the disease or condition is characterized by inappropriate lipid transfer or metabolism (e.g., atherosclerosis or gallstone formation). Such agents can also be used to modulate expression of a specific gene under the control of the SR-BI promoter in gene therapy. Moreover, the present invention provides diagnostic assays and reagents for determining whether a subject has a disorder involving, for example, aberrant expression of SR-BI genes. Other aspects of the invention are described below or will be apparent to one of skill in the art in light of the present disclosure.

4.2 Definitions

For convenience, the meaning of certain terms and phrases employed in the specification, examples, and appended claims are provided below.

The term "agonist", as used herein, is meant to refer to an agent (e.g. a transcription factor or enhancer molecule) that can directly or indirectly enhance, supplement or potentiate transcription from an SR-BI promoter.

The term "antagonist", as used herein, is meant to refer to an agent (e.g., repressor) that directly or indirectly prevents or suppresses transcription from an SR-BI promoter.

"Cells," "host cells" or "recombinant host cells" are terms used interchangeably herein. It is understood that such terms refer not only to the particular subject cell but to the progeny or potential progeny of such a cell. Because certain modifications may occur in succeeding generations due to either mutation or environmental influences, such progeny may not, in fact, be identical to the parent cell, but are still included within the scope of the term as used herein.

"Complementary" sequences or "complements" as used herein refer to sequences which have sufficient complementarity to be able to hybridize under appropriate conditions to a specified nucleic acid, thereby forming a stable duplex.

A "delivery complex" shall mean a targeting means (e.g. a molecule that results in higher affinity binding of a gene, protein, polypeptide or peptide to a target cell surface and/or increased cellular uptake by a target cell). Examples of targeting means include: sterols (e.g. cholesterol), lipids (e.g. a cationic lipid, virosome or liposome), viruses (e.g. adenovirus, adeno-associated virus, and retrovirus) or target cell specific binding agents (e.g., ligands recognized by target cell specific receptors). Preferred complexes are sufficiently stable in vivo to prevent significant uncoupling prior to internalization by the target cell. However, the complex is cleavable under appropriate conditions within the cell so that the gene, protein, polypeptide or peptide is released in a functional form.

As used herein, the term "gene" or "recombinant gene" refers to a nucleic acid molecule comprising an open reading frame and including at least one exon and (optionally) an intron sequence. The term "intron" refers to a DNA sequence present in a given gene which is not translated into protein and is generally found between exons.

As used herein, the term "transcriptional nucleic acid" refers to a nucleic acid that activates and/or regulates expression of a selected DNA sequence operably linked to the transcriptional nucleic acid, and which effects expression of the selected DNA sequence in cells. The term "5' flanking sequence" can include transcriptional nucleic acids, but is intended to refer more generally to any nucleic acid sequence located upstream of the transcription initiation site. Thus, a "5' flanking sequence" of an SR-BI gene is intended to include any nucleic acid sequence located upstream of the transcription initiation site and is not required to have any transcriptional activity. The term "basic promoter" as used herein is intended to refer to the minimal transcriptional nucleic acid that is capable of initiating transcription of a selected DNA sequence to which it is operably linked. The term "basic promoter" is intended to represent a promoter element providing basal transcription. A basic promoter frequently consists of a TATA box or TATA-like box and is bound by an RNA polymerase and by numerous transcription factors, such as Tfs and TATA box Binding Proteins (TBPs)

A "regulatory element", also termed herein "regulatory sequence" or "regulatory element" is intended to include elements which are capable of modulating transcription from a basic promoter and include elements such as enhancers and silencers. The term "enhancer", also referred to herein as "enhancer element", is intended to include regulatory elements capable of increasing, stimulating, or enhancing transcription from a basic promoter. The term "silencer", also referred to herein as "silencer element" is intended to include regulatory elements capable of decreasing, inhibiting, or repressing transcription from a basic promoter. Regulatory elements can also be present in genes other than in 5' flanking sequences. Thus, it is possible that SR-BI genes have regulatory elements located in introns, exons, coding regions, and 3' flanking sequences. Such regulatory elements are also intended to be encompassed by the present invention and can be identified by any of the assays that can be used to identify regulatory elements in 5' flanking regions of genes, such as those described herein.

The terms "basic promoter" and "regulatory element" further encompass "tissue specific" promoters and regulatory elements, i.e., promoters and regulatory elements which effect expression of the selected DNA sequence preferentially in specific cells (e.g., cells of a specific tissue). Gene expression occurs preferentially in a specific cell if expression in this cell type is significantly higher than expression in other cell types. The terms "promoter" and "regulatory element" also encompass so-called "leaky" promoters and "regulatory elements", which regulate expression of a selected DNA primarily in one tissue, but cause expression in other tissues as well. The terms "promoter" and "regulatory element" also encompass non-tissue specific promoters and regulatory elements, i.e., promoters and regulatory elements which are active in most cell types. Furthermore, a promoter or regulatory element can be a constitutive promoter or regulatory element, i.e., a promoter or regulatory element which constitutively regulates transcription, as opposed to a promoter or regulatory element which is inducible, i.e., a promoter or regulatory element which is active primarily in response to a stimulus. A stimulus can be, e.g., a molecule, such as a hormone, a cytokine, a heavy metal, phorbol esters, cyclic AMP (cAMP), or retinoic acid.

Regulatory elements are typically bound by transcription factors. The term "transcription factor" is intended to include proteins or modified forms thereof, which interact preferentially with specific nucleic acid sequences, i.e., regulatory elements, and which in appropriate conditions stimulate or repress transcription. Some transcription factors are active when they are in the form of a monomer. Alternatively, other transcription factors are active in the form of a dimer consisting of two identical proteins or different proteins (heterodimer). Modified forms of transcription factors are intended to refer to transcription factors having a postranslational modification, such as the attachment of a phosphate group. The activity of a transcription factor is frequently modulated by a postranslational modification. For example, certain transcription factors are active only if they are phosphorylated on specific residues. Alternatively, transcription factors can be active in the absence of phosphorylated residues and be inactivated by phosphorylation.

Examples of transcription factors that may bind to and regulate the human SR-BI promoter include SP1, AP2. An SP1 binding site is located at nucleotides 1534–1539 (GGGCGG) of SEQ ID NO: 1. AP2 binding sites are located at nucleotides 1473–1481 (GCCCCGGGC) and at nucleotides 1518–1526 (GCCCAAGGC) of SEQ ID NO: 1. Additional binding sites for transcription factors which were found in the sa-12 nucleic acid are shown in Table I. This Table shows transcription binding sites identified in the nucleic acid sa-12 by use of the publically available program TF SEARCH (http://www.genome.ad:jp/SIT/TFSEARCH htm1). Table I gives the nucleic acid sequence of the transcription binding sites ("SEQUENCE"), the name of the transcription factor binding specifically to these sequences ("TRANSCRIPTION FACTOR"), the orientation of the sequence, as sense ("S") or antisense ("AS"), the position of the sequences within the nucleic acid sequence shown in FIG. 1 (SEQ ID NO: 1) "POSITION", and the score ("SCORE"). The score is indicative of the homology of the transcription factor binding site sequence in the sa-12 nucleic acid to the binding site sequence of the same transcription factor given in the database (TFMATRIX transcription factor binding site profile database, supra). A score of 100 reflects complete sequence homology. Accordingly, it is possible to modulate transcription from an SR-BI promoter using compounds which modulate binding of such transcription factors to the SR-BI promoter or regulatory elements thereof.

TABLE I

| TRANSCRIPTION FACTOR | SEQUENCE | ORIENTATION | | POSITION | SCORE |
|---|---|---|---|---|---|
| Nkx-2 | TCAAGTG | S | | 129–135 | 100 |
| deltaE | CCTCACCTGGA | S | | 139–149 | 93.6 |
| USF | TCACGTGC | S | | 248–255 | 97.6 |
| USF | TCACGTGC | AS | | 248–255 | 92.8 |
| USF | TGCTCACGTGCTCA | AS | S | 245–258 | 91.8 |
| Nkx-2 | CACTTGC | AS | | 215–223 | 90.7 |
| SRY | TCTGTTT | AS | | 201–367 | 90.0 |
| MZF1 | AGTGGGGA | S | | 284–291 | 100.0 |
| SRY | TTTCTTT | AS | | 334–340 | 90 |
| SRY | TTTCTTT | AS | | 338–344 | 90 |
| SRY | TTTCTTT | AS | | 342–348 | 90 |
| SRY | TTTCTTT | AS | | 348–354 | 90 |
| SRY | TTTCTTT | AS | | 354–360 | 90 |
| SRY | TTTCTTT | AS | | 359–365 | 90 |
| GATA-2 | CGCTATCTCG | AS | | 421–430 | 97.2 |
| GATA-1 | CGCTATCTCG | AS | | 421–430 | 95.9 |
| GATA-3 | CGCTATCTC | AS | | 421–429 | 95.3 |
| Sox-5 | GTATTGTTAG | AS | | 532—541 | 98.0 |
| deltaE | CTCAGGTGATC | AS | | 591–601 | 92.6 |
| SREBP | CTCAGGTGATC | AS | | 591–601 | 91.0 |
| Lyf-1 | CCTCCCAAA | AS | | 623–631 | 100.0 |
| GATA-1 | GGTGATGGTG | S | | 913–922 | 97.6 |
| GATA-3 | AGGATAGGG | S | | 938–946 | 92.2 |
| GATA-2 | AAGGATAGGG | S | | 937–946 | 92.1 |
| GATA-2 | GCGGATACCT | S | | 951–960 | 94.1 |
| CdxA | CAGAATT | AS | | 968–974 | 92.1 |
| v-MYB | ACCGTTGTA | AS | | 1094–1102 | 92.5 |
| USF | GCATGTGG | AS | | 1086–1093 | 90.8 |
| GATA-1 | CCCGATAGAG | S | | 1168–1177 | 93.1 |
| GATA-2 | CCCGATAGAG | S | | 1168–1177 | 90.9 |
| GATA-1 | GATGATGGTC | S | | 1159–1168 | 90.6 |
| MZF1 | AGAGGGGA | S | | 1219–1226 | 94.8 |
| MZF1 | GGAGGGGA | S | | 1136–1243 | 93.0 |
| Sp1 | GCCCCGCCCC | AS | | 1419–1428 | 94.5 |
| Sp1 | ACCCCGCCCC | AS | | 1468–1477 | 100.0 |
| Sp1 | GCCCGCCCC | AS | | 1446–1455 | 94.5 |
| Sp1 | TCCCCGCCCC | AS | | 1457–1466 | 95.9 |
| Sp1 | GGCCCGCCCC | AS | | 1490–1500 | 94.5 |
| MZF1 | TCCCCGCC | AS | | 1456–1464 | 93 |
| GATA-1 | GGCGATGGGG | S | | 1552–1561 | 98.4 |
| CdxA | CATAAAAA | AS | | 1562–1568 | 92.1 |
| E47 | CTGGCCACCTGCCGG | AS | | 1572–1586 | 92.3 |
| GATA-2 | CGCGATGGGG | S | | 1551–1561 | 90.5 |

Another publically available database of transcription factors and the sequences to which they bind is available from the National Library of Medicine in the "Transcription Data Base".

A nucleic acid is transcribed from a promoter if it is operably linked to the promoter. The term "operably linked" is intended to mean that the promoter is associated with the nucleic acid in such a manner as to facilitate transcription of the nucleic acid from the promoter.

"Homology" or "identity" or "similarity" refers to sequence similarity between two peptides or between two nucleic acid molecules. Homology can be determined by comparing a position in each sequence which may be aligned for purposes of comparison. When a position in the compared sequence is occupied by the same base or amino acid, then the molecules are homologous at that position. A degree of homology between sequences is a function of the number of matching or homologous positions shared by the sequences. An "unrelated" or "non-homologous" sequence shares less than 40% identity, though preferably less than 25% identity, with one of the sequences of the present invention.

The term "interact" as used herein is meant to include detectable interactions between molecules, such as can be detected using, for example, a yeast two hybrid assay. The term interact is also meant to include "binding" interactions between molecules. Interactions may be, for example, protein-protein, protein-nucleic acid, protein-small molecule or small molecule-nucleic acid in nature.

The term "isolated" as used herein with respect to nucleic acids, such as DNA or RNA, refers to molecules separated from other DNAs or RNAs, respectively, that are present in the natural source of the macromolecule. The term isolated as used herein also refers to a nucleic acid or peptide that is substantially free of cellular material, viral material, or culture medium when produced by recombinant DNA techniques, or chemical precursors or other chemicals when chemically synthesized. Moreover, an "isolated nucleic acid" is meant to include nucleic acid fragments which are not naturally occurring as fragments and would not be found in the natural state. The term "isolated" is also used herein to refer to polypeptides which are isolated from other cellular proteins and is meant to encompass both purified and recombinant polypeptides.

The term "lipid" shall refer to a fat or fat-like substance that is insoluble in polar solvents such as water. Including true fats (e.g. esters of fatty acids and glycerol); lipids (phospholipids, cerebrosides, waxes); sterols (cholesterol, ergosterol) and lipoproteins (e.g. HDL, LDL and VLDL).

The term "modulation" as used herein refers to both upregulation, (i.e., activation or stimulation), for example by agonizing; and downregulation (i.e. inhibition or suppression), for example by antagonizing of a bioactivity (e.g. expression of a gene).

The "non-human animals" of the invention include mammals such as rodents, non-human primates, sheep, goats, horses, dogs, cows, chickens, or amphibians, reptiles, etc. Preferred non-human animals are selected from the rodent family including rat and mouse, most preferably mouse, though transgenic amphibians, such as members of the Xenopus genus, and transgenic chickens can also provide important tools for understanding and identifying agents which can affect, for example, embryogenesis and tissue formation. The term "chimeric animal" is used herein to refer to animals in which an exogenous sequence is found, or in which an exogenous sequence is expressed in some but not all cells of the animal. The term "tissue-specific chimeric animal" indicates that an exogenous sequence is present and/or expressed or disrupted in some tissues, but not others.

As used herein, the term "nucleic acid" refers to polynucleotides such as deoxyribonucleic acid (DNA), and, where appropriate, ribonucleic acid (RNA). The term should also be understood to include, as equivalents, derivatives, variants and analogs of either RNA or DNA made from nucleotide analogs, and, as applicable to the embodiment being described, single (sense or antisense) and double-stranded polynucleotides.

The terms "protein", "polypeptide" and "peptide" are used interchangeably herein when referring to a gene product.

The term "recombinant protein" refers to a polypeptide which is produced by recombinant DNA techniques, wherein generally, DNA encoding the polypeptide is inserted into a suitable expression vector which is in turn used to transform a host cell to produce the heterologous protein.

"Small molecule" as used herein, is meant to refer to a composition, which has a molecular weight of less than about 5 kD and most preferably less than about 4 kD. Small molecules can be nucleic acids, peptides, polypeptides, peptidomimetics, carbohydrates, lipids or other organic (carbon containing) or inorganic molecules. Many pharmaceutical companies have extensive libraries of chemical and/or biological mixtures, often fungal, bacterial, or algal extracts, which can be screened with any of the assays of the invention.

As used herein, the term "specifically hybridizes" or "specifically detects" refers to the ability of a nucleic acid molecule of the invention to hybridize to at least approximately 6, 12, 20, 30, 40, 50, 60, 70, 80, 90, 100, 110, 120, 130 or 140 consecutive nucleotides of an SR-BI promoter or a sequence complementary thereto.

"SR-BI" or "SR-BI receptor" refers to a class B scavenger receptor that has been shown to bind HDL cholesterol and mediate uptake into cells (Acton, S. et al., *Science* 271:518–520). SR-BI has also been shown to bind with high affinity to modified proteins (e.g. acetylated LDL, oxidized LDL, maleylated bovine serum albumin) and native LDL (Acton, et al., (1994) *J. Biochem.* 269:21003–21009). Further, SR-BI has been shown to bind anionic phospholipids, such as phosphatidylserine and phosphatidylinositol, but not zwitterionic phospholipids, such as phosphatidylcholine, phosphatidylethanolamine and sphingomyelin. Competition studies suggest that anionic phospholipids bind to SR-BI at a site close to or identical with the sites of native and modified LDL binding and that the interaction may involve polyvalent binding via multiple anionic phospholipid molecules (Rigotti, A.., S. Acton and M. Krieger (1995) *J. Biochem* 270:16221–16224). The human SR-BI protein is described in Calvo et al. (1993) J. Biol. Chem. 268:18929 and hamster SR-BI is described in International Patent Application Number WO 96/00288 entitled "Class B1 and C1 Scavenger Receptors" by Acton, S. et al.

The term "SR-BI activity" is intended to encompass any activity of an SR-BI protein or SR-BI receptor, such as those described in the previous paragraph, as well as activities which are mediated by SR-BI. Thus, SR-BI activity is intended to include binding activity, such as binding of a molecule, e.g., a lipid, to SR-BI. The term "aberrant SR-BI activity" or "abnormal SR-BI activity" is intended to encompass an activity of SR-BI which differs from the same SR-BI activity in a healthy subject. An aberrant SR-BI activity can result, e.g., from a mutation in the protein, which results, e.g., in lower or higher binding affinity of a lipid to the mutated SR-BI. An aberrant SR-BI activity can also result from a lower or higher level of SR-BI receptor on cells, which can result, e.g., from a mutation in the SR-BI 5' flanking region of the SR-BI gene. Accordingly, an aberrant SR-BI activity can result from an abnormal SR-BI promoter activity. The terms "abnormal SR-BI promoter activity" "aberrant SR-BI promoter activity","abnormal SR-BI transcriptional activity" and "aberrant SR-BI transcriptional activity", which are used interchangeably herein, refer to the transcriptional activity of an SR-BI promoter which differs from the transcriptional activity of the same promoter in a healthy subject. An abnormal SR-BI activity can result from a higher or lower transcriptional activity than that in a healthy subject. An aberrant SR-BI promoter activity can result, e.g., from the presence of a genetic lesion in a promoter region, such as in a regulatory element located in the promoter. An "aberrant SR-BI promoter activity" is also intended to refer to the transcriptional activity of an SR-BI promoter which is functional (capable of inducing transcription of a gene to which it is operably linked) in tissues or cells in which the "natural" or wild-type SR-BI promoter is not functional or which is non functional in tissues or cells in which the "natural" or wild-type SR-BI promoter is non-functional. Thus, a tissue distribution of SR-BI in a subject which differs from the tissue distribution of SR-BI in a "normal" or "healthy" subject, can be the result of an abnormal transcriptional activity from the SR-BI promoter region. Such an abnormal transcriptional activity can result, e.g., from one or more mutations in a promoter region, such as in a regulatory element thereof. An abnormal transcriptional activity can also result from a mutation in a transcription factor involved in the control of SR-BI gene expression.

As used herein, the term "transfection" means the introduction of a nucleic acid, e.g., an expression vector, into a recipient cell by nucleic acid-mediated gene transfer. The term "transduction" is generally used herein when the transfection with a nucleic acid is by viral delivery of the nucleic acid. "Transformation", as used herein, refers to a process in which a cell's genotype is changed as a result of the cellular uptake of exogenous DNA or RNA, and, for example, the transformed cell expresses a recombinant form of a polypeptide or, in the case of anti-sense expression from the transferred gene, the expression of a naturally-occurring form of the recombinant protein is disrupted.

As used herein, the term "transgene" refers to a nucleic acid sequence which has been introduced into a cell. Daughter cells deriving from a cell in which a transgene has been introduced are also said to contain the transgene (unless it has been deleted). A transgene can encode, e.g., a polypeptide, or an antisense transcript, partly or entirely heterologous, i.e., foreign, to the transgenic animal or cell into which it is introduced, or, is homologous to an endogenous gene of the transgenic animal or cell into which it is introduced, but which is designed to be inserted, or is inserted, into the animal's genome in such a way as to alter the genome of the cell into which it is inserted (e.g., it is inserted at a location which differs from that of the natural gene or its insertion results in a knockout). Alternatively, a transgene can also be present in an episome. A transgene can include one or more transcriptional regulatory sequences and any other nucleic acid, (e.g. intron), that may be necessary for optimal expression of a selected nucleic acid.

A "transgenic animal" refers to any animal, preferably a non-human animal, e.g. a mammal, bird or an amphibian, in which one or more of the cells of the animal contain heterologous nucleic acid introduced by way of human intervention, such as by transgenic techniques well known in the art. The nucleic acid is introduced into the cell, directly or indirectly by introduction into a precursor of the cell, by way of deliberate genetic manipulation, such as by microinjection or by infection with a recombinant virus. The term genetic manipulation does not include classical crossbreeding, or in vitro fertilization, but rather is directed to the introduction of a recombinant DNA molecule. This molecule may be integrated within a chromosome, or it may be extrachromosomally replicating DNA. In the typical transgenic animals described herein, the transgene causes cells to express a recombinant form of one of a protein, e.g. either agonistic or antagonistic forms. However, transgenic animals in which the recombinant gene is silent are also contemplated, as for example, the FLP or CRE recombinase dependent constructs described below. Moreover, "transgenic animal" also includes those recombinant animals in which gene disruption of one or more genes is caused by human intervention, including both recombination and antisense techniques.

The term "treating" as used herein is intended to encompass curing as well as ameliorating at least one symptom of the condition or disease.

As used herein, the term "vector" refers to a nucleic acid molecule capable of transporting another nucleic acid to which it has been linked. One type of preferred vector is an episome, i.e., a nucleic acid capable of extra-chromosomal replication. Preferred vectors are those capable of autonomous replication and/or expression of nucleic acids to which they are linked. Vectors capable of directing the expression of genes to which they are operatively linked are referred to herein as "expression vectors". In general, expression vectors of utility in recombinant DNA techniques are often in the form of "plasmids" which refer generally to circular double stranded DNA loops which, in their vector form are not bound to the chromosome. In the present specification, "plasmid" and "vector" are used interchangeably as the plasmid is the most commonly used form of vector. However, the invention is intended to include such other forms of expression vectors which serve equivalent functions and which become known in the art subsequently hereto.

4.3 Nucleic Acids of the Present Invention

As described below, one aspect of the invention pertains to isolated transcriptional nucleic acids selected from the group consisting of a nucleic acid having SEQ ID NO: 1, a nucleic acid having ATCC Deposit No. 98304, or ATCC Deposit No. 97907 fragments thereof, functional fragments thereof, SR-BI basic promoters, SR-BI regulatory elements, equivalents to any of these nucleic acids, and complements to any of these nucleic acids. The invention also pertains to nucleic acids capable of hybridizing to the complement of the nucleic acid sequence shown in FIG. 1 (SEQ ID NO: 1) or to the complement of nucleic acid having ATCC Deposit No. 98304 or ATCC Deposit No. 97907. Also within the scope of the invention are nucleic acids which are homologous, e.g., 85% homologous to any of the above-recited nucleic acids. Accordingly, the invention provides nucleic acids which are capable of functioning as a promoter, nucleic acids which are capable of functioning as a regulatory element, as well as nucleic acids which have not been shown to function as either. A "functional" fragment of a nucleic acid as used herein is a nucleic acid fragment capable of modulating transcription of a gene operably linked to the fragment. Thus, a "functional fragment" of a nucleic acid is intended to include nucleic acids capable of functioning as a promoter or as a regulatory element in appropriate conditions. The term equivalent of a nucleic acid is understood to include nucleotic acids which differ by one or more nucleotide substitutions, additions or deletions from the nucleic acid and which has a similar activity as the nucleic acid.

Preferred nucleic acids of the invention are from vertebrate genes encoding SR-BI receptors. Particularly preferred vertebrate nucleic acids are mammalian nucleic acids. A particularly preferred nucleic acid of the invention is a human nucleic acid, such as a nucleic acid having SEQ ID NO: 1 or a portion thereof. Regardless of species, particularly preferred nucleic acids are at least 80%, 85% 90%, 95% or 99% similar or identical to the nucleic acids shown in any of SEQ ID Nos: 1 or 2.

Accordingly, a preferred embodiment of the invention encompasses isolated nucleic acid molecules having a nucleotide sequence corresponding to at least a portion of the nucleic acid having ATCC Deposit No. 98304 or ATCC Deposit No. 97907. In an even more preferred embodiment of the invention, the isolated nucleic acid comprises a nucleotide sequence corresponding to a functional portion or fragment of the nucleic acid having ATCC Deposit No.

98304, such that upon operably linking such a nucleic acid fragment to a second nucleic acid capable of being transcribed, the second nucleic acid can be transcribed. The functional portion of the nucleic acid, which can have the activity of a promoter or a regulatory element, can be a portion of the nucleic acid which provides tissue specific expression. A preferred portion of the nucleic acid provides tissue specific expression substantially similar to the tissue distribution of SR-BI. Accordingly, a preferred portion of a nucleic acid having SEQ ID NO: 1 or having ATCC Deposit No. 98304 is a portion which modulates transcription preferentially in ovaries, adrenals, liver, and placenta. However, portions of a nuleic acid which modulate transcription in only some of these tissues, or tissues other than ovaries, adrenals, liver and placenta are also within the scope of the invention. In fact, it is likely that tissue specificity is determined by several regulatory elements in the SR-BI promoter. Accordingly, a portion of the promoter may modulate transcription only in certain tissues. Similarly, portions of the nucleic acid having ATCC Deposit No. 98304 or SEQ ID NO: 1, which constitutively enhance or repress transcription are also within the scope of the invention. Additional preferred portions of an SR-BI promoter include those which contain an inducible element.

Other preferred nucleic acids of the invention are nucleic acids corresponding to one or more discrete regulatory elements, such as enhancers and silencers. Particularly preferred nucleic acids contained in nucleic acid having ATCC Deposit No. 98304, comprise one or more of the potential transcription factor binding sites, such as those identified in the TF Search, and shown in Table I. Accordingly, isolated nucleic acids of the invention also encompass those which do not contain a basic promoter. As set forth above, nucleic acids comprising one or more regulatory elements can provide tissue specific expression, including tissue specific expression other than that of the "natural" SR-BI gene, provide constitutive enhancement or repression of transcription, or inducible enhancement or repression of transcription.

Thus, in one embodiment of the invention, an isolated nucleic acid deriving from an SR-BI promoter comprises a nucleic acid sequence from about nucleic acid residue 1534 to about nucleic acid residue 1595 of SEQ ID NO: 1. Other preferred isolated nucleic acids comprise a nucleic acid sequence from about nucleic acid residue900 to about nucleic acid residue 1595, from about nucleic acid residue 610 to about nucleic acid residue 1595, from about nucleic acid residue 500 to about nucleic acid residue 1595, from about nucleic acid residue 400 to about nucleic acid residue 1595, from about nucleic acid residue 300 to about nucleic acid residue 1595, from about nucleic acid residue 200 to about nucleic acid residue 1595, from about nucleic acid residue 100 to about nucleic acid residue 1595, from about nucleic acid residue 1 to about nucleic acid residue 1595, of SEQ ID NO: 1.

Any nucleic acid fragment of the invention can be prepared according to methods well known in the art and described, e.g., in Sambrook, J. Fritsch, E. F., and Maniatis, T. (1989) *Molecular Cloning: A Laboratory Manual,* Cold Spring Harbor Laboratory Press, Cold Spring Harbor, N.Y. For example, discrete fragments of the promoter can be prepared and cloned using restriction enzymes. Alternatively, discrete fragments can be prepared using the Polymerase Chain Reaction (PCR) using primers having an appropriate sequence, such as a sequence in SEQ ID NO: 1. The activity of promoter fragments can be tested in vitro in transfection assays or in vivo in transgenic animals as described in the Examples.

Also within the scope of the invention are nucleic acids which are homologues or equivalents of the above-described nucleic acids.

In yet another embodiment of the invention, the isolated nucleic acid comprises a nucleic acid sequence of SEQ ID NO: 1 or portion thereof which has been modified, e.g., by adding, deleting, or substituting one or more nucleic acid residues. Such modifications can modulate the trancriptional activity of the SR-BI promoter or regulatory element. For example, a modification can increase or decrease the activity of a promoter or regulatory element. A modification can also affect the tissue specificity of a promoter or regulatory element. Thus, for example, an SR-BI promoter or regulatory element can be modified to stimulate transcription in only one of the tissues in which it is normally expressed. An SR-BI promoter or regulatory element can also be modified to be inducible by a desired drug, for example by creating in the sequence a site that is inducible by the specific drug.

Desired modifications of an SR-BI promoter or regulatory element can be performed according to methods well known in the art, such as by mutagenesis. The activity of the modified promoter or regulatory element can then be tested, e.g., by cloning the modified promoter upstream of a reporter gene, transfecting hte construct and measuring of the level of expression of the reporter construct. The activity of the modified promoter or regulatory element can also be analyzed in vivo in transgenic animals. Such methods are further described in the Examples. It is also possible to create libraries of modified fragments which can be screened using a functional assay, in which, for example, only modified promoters or regulatory elements having the desired activity are selected. These assays can be based, e.g., on the use of reporter genes providing resistance to specific drugs, e.g., G418. Selection of cells having a reporter construct containing a promoter or regulatory element having the desired modification can be isolated by culture in the presence of the drug.

Another aspect of the invention provides a nucleic acid which hybridizes under stringent conditions to the nucleic acid shown in SEQ ID No: 1 or complement thereof. Appropriate stringency conditions which promote DNA hybridization, for example, 6.0×sodium chloride/sodium citrate (SSC) at about 45° C., followed by a wash of 2.0×SSC at 50 ° C., are known to those skilled in the art or can be found in *Current Protocols in Molecular Biology,* John Wiley & Sons, N.Y. (1989), 6.3.1–6.3.6. For example, the salt concentration in the wash step can be selected from a low stringency of about 2.0×SSC at 50° C. to a high stringency of about 0.2×SSC at 50° C. In addition, the temperature in the wash step can be increased from low stringency conditions at room temperature, about 22° C., to high stringency conditions at about 65° C. Both temperature and salt may be varied, or temperature or salt concentration may be held constant while the other variable is changed. In a preferred embodiment, a nucleic acid of the present invention will bind to SEQ ID No. 1 under moderately stringent conditions, for example at about 2.0×SSC and about 40° C. In a particularly preferred embodiment, a nucleic acid of the present invention will bind to SEQ ID No: 1 or complement thereof under high stringency conditions.

Hybridization can be used to isolate nucleic acids corresponding to 5' flanking regions of SR-BI genes from various animal species. A comparison of these nucleic acids should be indicative of regions involved in the regulation of expression of the SR-BI gene, since these regions are expected to be conserved among various species.

Also within the scope of the invention are nucleic acids comprising an SR-BI promoter or regulatory element, e.g, having a nucleotide sequence of SEQ ID NO: 1, operably linked to a nucleic acid to be transcribed. The SR-BI promoter or regulatory element can be, e.g., any of the above-described fragments of the nucleic acid having ATCC Deposit No. 98304, any nucleic fragments having a sequence from SEQ ID No: 1, or modified form thereof. The SR-BI promoter can also be a combination of several fragments or regulatory elements having a sequence from SEQ ID NO: 1 or modified form thereof, as well as multimers of one or more of these fragments or regulatory elements or modified form thereof The promoter can also contain regulatory elements derived from other genes.

In one embodiment, the nucleic acid to be transcribed encodes a protein or peptide. The protein can be any protein useful in gene therapy, including, but not limited to, cytokines, structural proteins, receptors, transcription factors. In a preferred embodiment, the protein to be expressed in SR-BI. In another embodiment, the nucleic acid is transcribed into a nucleic acid which is antisense to a desired nucleic acid sequence. Expression of antisense nucleic acids can be used, e.g., to reduce or inhibit translation of a mRNA into a specific protein. In a specific embodiment, the antisense molecule hybridizes to the SR-BI gene and reduces or inhibits expression of the SR-BI gene. Such methods are also useful in gene therapy methods.

In yet another embodiment, the nucleic acid to be transcribed from an SR-BI promoter, fragment or modified form thereof, is a reporter gene. Reporter genes include any gene encoding a protein, the amount of which can be determined. Preferred reporter genes include the luciferase gene, the beta-galactosidase gene (LacZ), the chloramphenicol acetyl transferase (CAT) gene, or any gene encoding a protein providing resistance to a specific drug.

A preferred nucleic acid containing a nucleic acid to be transcribed under the control of an SR-BI promoter or regulatory element comprises a nucleic acid having SEQ ID NO: 1 operably linked to the bacterial luciferase gene, e.g., the luciferase gene present in pGL3-basic. Another preferred nucleic acid of the invention comprises a nucleic acid having SEQ ID NO: 1 operably linked to the bacterial beta-galactosidase gene (LacZ). Yet another preferred nucleic acid comprises a nucleic acid having SEQ ID NO: 1 operably linked to a "Neo" gene providing resistance to the drug G418.

The nucleic acid to be transcribed can be operably linked to an SR-BI promoter, fragment or modified form thereof using methods well known in the art.

4.3.1. Vectors

This invention also provides expression vectors comprised of the instant described nucleic acids operably linked to a nucleic acid to be transcribed, e.g., a gene. In one embodiment, the expression vector includes a recombinant gene encoding an SR-BI receptor. Such expression vectors can be used to transfect cells and thereby produce protein. Moreover, the gene constructs of the present invention can also be used as a part of a gene therapy protocol to deliver nucleic acids in vitro or in vivo. Thus, another aspect of the invention features expression vectors for in vivo or in vitro transfection and expression of genes in particular cell types (e.g. liver, adrenals, ovary, placenta).

A preferred approach for in vivo introduction of nucleic acid into a cell is by use of a viral vector containing nucleic acid, e.g. a cDNA, under the control of an SR-BI promoter or regulatory element. Infection of cells with a viral vector has the advantage that a large proportion of the targeted cells can receive the nucleic acid. Additionally, molecules encoded within the viral vector, e.g., by a cDNA contained in the viral vector, are expressed efficiently in cells which have taken up viral vector nucleic acid.

Retrovirus vectors and adeno-associated virus vectors are generally understood to be the recombinant gene delivery system of choice for the transfer of exogenous genes in vivo, particularly into humans. These vectors provide efficient delivery of genes into cells, and the transferred nucleic acids are stably integrated into the chromosomal DNA of the host. A major prerequisite for the use of retroviruses is to ensure the safety of their use, particularly with regard to the possibility of the spread of wild-type virus in the cell population. The development of specialized cell lines (termed "packaging cells") which produce only replication-defective retroviruses has increased the utility of retroviruses for gene therapy, and defective retroviruses are well characterized for use in gene transfer for gene therapy purposes (for a review see Miller, A. D. (1990) Blood 76:271). Thus, recombinant retrovirus can be constructed in which part of the retroviral coding sequence (gag, pol, env) and promoter and/or regulatory elements have been replaced by nucleic acid encoding comprising an SR-BI promoter or regulatory element and a nucleic acid encoding a protein of choice, rendering the retrovirus replication defective. The replication defective retrovirus is then packaged into virions which can be used to infect a target cell through the use of a helper virus by standard techniques. Protocols for producing recombinant retroviruses and for infecting cells in vitro or in vivo with such viruses can be found in Current Protocols in Molecular Biology, Ausubel, F. M. et al. (eds.) Greene Publishing Associates, (1989), Sections 9.10–9.14 and other standard laboratory manuals. Examples of suitable retroviruses include pLJ, pZIP, pWE and pEM which are well known to those skilled in the art. Examples of suitable packaging virus lines for preparing both ecotropic and amphotropic retroviral systems include ψCrip, ψCre, ψ2 and ψAm. Retroviruses have been used to introduce a variety of genes into many different cell types, including hepatic cells, in vitro and/or in vivo (see for example Eglitis, et al. (1985) Science 230:1395–1398; Danos and Mulligan (1988) Proc. Natl. Acad. Sci. USA 85:6460–6464; Wilson et al. (1988) Proc. Natl. Acad. Sci. USA 85:3014–3018; Armentano et al. (1990) Proc. Natl. Acad. Sci. USA 87:6141–6145; Huber et al. (1991) Proc. Natl. Acad. Sci. USA 88:8039–8043; Ferry et al. (1991) Proc. Natl. Acad. Sci. USA 88:8377–8381; Chowdhury et al. (1991) Science 254:1802–1805; van Beusechem et al. (1992) Proc. Natl. Acad. Sci. USA 89:7640–7644; Kay et al. (1992) Human Gene Therapy 3:641–647; Dai et al. (1992) Proc. Natl. Acad. Sci. USA 89:10892–10895; Hwu et al. (1993) J. Immunol. 150:4104–4115; U.S. Pat. No. 4,868,116; U.S. Pat. No. 4,980,286; PCT Application WO 89/07136; PCT Application WO 89/02468; PCT Application WO 89/05345; and PCT Application WO 92/07573).

Furthermore, it has been shown that it is possible to limit the infection spectrum of retroviruses and consequently of retroviral-based vectors, by modifying the viral packaging proteins on the surface of the viral particle (see, for example PCT publications WO93/25234 and WO94/06920). For instance, strategies for the modification of the infection spectrum of retroviral vectors include: coupling antibodies specific for cell surface antigens to the viral env protein (Roux et al. (1989) PNAS 86:9079–9083; Julan et al. (1992) J. Gen Virol 73:3251–3255; and Goud et al. (1983) Virology 163:251–254); or coupling cell surface receptor ligands to the viral env proteins (Neda et al. (1991) J Biol Chem 266:14143–14146). Coupling can be in the form of the chemical cross-linking with a protein or other variety (e.g. lactose to convert the env protein to an asialoglycoprotein), as well as by generating fusion proteins (e.g. single-chain antibody/env fusion proteins). This technique, while useful to limit or otherwise direct the infection to certain tissue types, can also be used to convert an ecotropic vector in to an amphotropic vector.

Another viral gene delivery system useful in the present invention utilitizes adenovirus-derived vectors. The genome of an adenovirus can be manipulated such that it encodes and expresses a gene product of interest under the control of an SR-BI promoter or regulatory element, but is inactivated in terms of its ability to replicate in a normal lytic viral life cycle. See for example Berkner et al. (1988) *BioTechniques* 6:616; Rosenfeld et al. (1991) *Science* 252:431–434; and Rosenfeld et al. (1992) *Cell* 68:143–155. Suitable adenoviral vectors derived from the adenovirus strain Ad type 5 dl324 or other strains of adenovirus (e.g., Ad2, Ad3, Ad7 etc.) are well known to those skilled in the art. Recombinant adenoviruses can be advantageous in certain circumstances in that they are not capable of infecting nondividing cells and can be used to infect a wide variety of cell types, including epithelial cells (Rosenfeld et al. (1992) cited supra). Furthermore, the virus particle is relatively stable and amenable to purification and concentration, and as above, can be modified so as to affect the spectrum of infectivity. Additionally, introduced adenoviral DNA (and foreign DNA contained therein) is not integrated into the genome of a host cell but remains episomal, thereby avoiding potential problems that can occur as a result of insertional mutagenesis in situations where introduced DNA becomes integrated into the host genome (e.g., retroviral DNA). Moreover, the carrying capacity of the adenoviral genome for foreign DNA is large (up to 8 kilobases) relative to other gene delivery vectors (Berkner et al. cited supra; Haj-Ahmand and Graham (1986) *J. Virol.* 57:267). Most replication-defective adenoviral vectors currently in use and therefore favored by the present invention are deleted for all or parts of the viral E1 and E3 genes but retain as much as 80% of the adenoviral genetic material (see, e.g., Jones et al. (1979) *Cell* 16:683; Berkner et al., supra; and Graham et al. in *Methods in Molecular Biology*, E. J. Murray, Ed. (Humana, Clifton, N.J., 1991) vol. 7. pp. 109–127).

Yet another viral vector system useful for delivery of a gene under the control of an SR-BI promoter or regulatory element thereof is the adeno-associated virus (AAV). Adeno-associated virus is a naturally occurring defective virus that requires another virus, such as an adenovirus or a herpes virus, as a helper virus for efficient replication and a productive life cycle. (For a review see Muzyczka et al. *Curr. Topics in Micro. and Immunol.* (1992) 158:97–129). It is also one of the few viruses that may integrate its DNA into non-dividing cells, and exhibits a high frequency of stable integration (see for example Flotte et al. (1992) *Am. J. Respir. Cell. Mol. Biol.* 7:349–356; Samulski et al. (1989) *J. Virol.* 63:3822–3828; and McLaughlin et al. (1989) *J. Virol.* 62:1963–1973). Vectors containing as little as 300 base pairs of AAV can be packaged and can integrate. Space for exogenous DNA is limited to about 4.5 kb. An AAV vector such as that described in Tratschin et al. (1985) *Mol. Cell. Biol.* 5:3251–3260 can be used to introduce DNA into cells. A variety of nucleic acids have been introduced into different cell types using AAV vectors (see for example Hermonat et al. (1984) *Proc. Natl. Acad. Sci. USA* 81:6466–6470; Tratschin et al. (1985) *Mol. Cell. Biol.* 4:2072–2081; Wondisford et al. (1988) *Mol. Endocrinol.* 2:32–39; Tratschin et al. (1984) *J. Virol.* 51:611–619; and Flotte et al. (1993) *J. Biol. Chem.* 268:3781–3790).

In a representative embodiment, a gene under the control of an SR-BI promoter or regulatory element can be entrapped in liposomes bearing positive charges on their surface (e.g., lipofectins) and (optionally) which are tagged with antibodies against cell surface antigens of the target tissue (Mizuno et al. (1992) *No Shinkei Geka* 20:547–551; PCT publication WO91/06309; Japanese patent application 1047381; and European patent publication EP-A-43075). For example, lipofection of cells can be carried out using liposomes tagged with monoclonal antibodies against any cell surface antigen present on an hepatic cell, such as an asialoglycoprotein receptor.

In addition to viral transfer methods, such as those illustrated above, non-viral methods can also be employed to cause expression of a gene, which is under the control of a subject promoter in the tissue of an animal. Most nonviral methods of gene transfer rely on normal mechanisms used by mammalian cells for the uptake and intracellular transport of macromolecules. In preferred embodiments, non-viral targeting means of the present invention rely on endocytic pathways for the uptake of genes by the targeted cell. Exemplary targeting means of this type include liposomal derived systems, poly-lysine conjugates, and artificial viral envelopes.

4.3.2. Probes and Primers

Moreover, the SR-BI promoter nucleic acid sequences provide for the generation of probes and primers which can be used, e.g.; in diagnostic assays. For instance, the present invention also provides a probe/primer comprising a substantially purified oligonucleotide, which oligonucleotide comprises a region of nucleotide sequence that hybridizes under stringent conditions to at least approximately 6, 8, 10 or 12, preferably about 25, 30, 40, 50 or 75 consecutive nucleotides of SEQ ID No: 1.

In preferred embodiments, the probe further comprises a label attached thereto, which is capable of being detected, e.g. the label group is selected from amongst radioisotopes, fluorescent compounds, enzymes, and enzyme co-factors.

As discussed in more detail below, such probes can also be used as a part of a diagnostic test kit, for example, to detect mutations in the promoter, which result in faulty expression of an SR-BI receptor.

4.3.3. Antisense and Triplex Techniques

Another aspect of the invention relates to the use of the isolated nucleic acid in "antisense" therapy. As used herein, "antisense" therapy refers to administration or in situ generation of oligonucleotide molecules or their derivatives which specifically hybridize (e.g. bind) under cellular conditions, to a nucleic acid, such as an RNA or an SR-BI transcriptional nucleic acid, so as to suppress translation of the RNA or initiation of gene transcription, respectively. Antisense molecules can be used, e.g., in gene therapy methods in which inhibition of production of a gene product is desired. The binding may be by conventional base pair complementarity, or, for example, in the case of binding to DNA duplexes, through specific interactions in the major groove of the double helix. In general, "antisense" therapy refers to the range of techniques generally employed in the art, and includes any therapy which relies on specific binding to oligonucleotide sequences.

An antisense construct of the present invention can be delivered, for example, as an expression plasmid which, when transcribed in the cell, produces RNA which is complementary to at least a unique portion of the SR-BI transcriptional nucleic acid. Alternatively, the antisense construct is an oligonucleotide probe which is generated ex vivo and which, when introduced into the cell suppresses the initiation of expression from an SR-BI promoter. Such oligonucleotide probes are preferably modified oligonucleotides which are resistant to endogenous nucleases, e.g. exonucleases and/or endonucleases, and are therefore stable in vivo. Exemplary nucleic acid molecules for use as antisense oligonucleotides are phosphoramidate, phosphothioate and methylphosphonate analogs of DNA (see also U.S. Pat. Nos. 5,176,996; 5,264,564; and 5,256,775). Additionally, general approaches to constructing oligomers useful in antisense therapy have been reviewed, for example, by Van der Krol et al. (1988) *Biotechniques* 6:958–976; and Stein et al. (1988) *Cancer Res* 48:2659–2668.

Antisense approaches involve the design of oligonucleotides (either DNA or RNA) that are complementary, e.g., to portions of an RNA molecule or to portions of SR-BI promoter (e.g. portions to which a transcriptional regulatory molecule binds). The RNA molecule can be, e.g., transcribed from a gene encoding a transcriptional regulatory molecule of an SR-BI promoter or regulatory element, such that antisense oligonucleotide binding prevents or suppresses the production of transcription factors, resulting in inhibition of transcription from the SR-BI promoter. Absolute complementarity, although preferred, is not required. A sequence "complementary" to a portion of a nucleic acid, as referred to herein, means a sequence having sufficient complementarity to be able to hybridize with the nucleic acid, forming a stable duplex; in the case of double-stranded antisense nucleic acids, a single strand of the duplex DNA may thus be tested, or triplex formation may be assayed. The ability to hybridize will depend on both the degree of complementarity and the length of the antisense nucleic acid. Generally, the longer the hybridizing nucleic acid, the more base mismatches with an RNA it may contain and still form a stable duplex (or triplex, as the case may be). One skilled in the art can ascertain a tolerable degree of mismatch by use of standard procedures to determine the melting point of the hybridized complex. Antisense nucleic acids should be at least six nucleotides in length, and are preferably less that about 100 and more preferably less than about 50, 25, 17 or 10 nucleotides in length. Preferred antisense nucleic acids bind to the transcription factor binding sites shown in Table 1.

Even more preferred antisense nucleic acids are single stranded nucleic acids having the following nucleic acid sequence:

| | |
|---|---|
| 5' GCCAGTGGTTTTATGCCCCA 3' | ((SEQ ID NO: 4) complement of nucleic acid residues 1557–1576 of SEQ ID NO: 1 including the TATA box); |
| 5' GGAGCAGCCCGGCAGGTG 3' | ((SEQ ID NO: 5) complement of nucleic acid residues 1577–1594 of SEQ ID NO: 1); |
| 5' CGCCGGGCCGCCCCCGGGCA 3' | (SEQ ID NO: 6) complement of nucleic acid residues 1527–1546 of SEQ ID NO: 1); and |
| 5' AGCGGGCCCGGGGCGGGGTG 3' | (SEQ ID NO: 7) complement of nucleic acid residues 1467–1486 of SEQ ID NO: 1). |

Regardless of the choice of target sequence, it is preferred that in vitro studies are first performed to quantitate the ability of the antisense oligonucleotide to inhibit the activation of gene expression. It is preferred that these studies utilize controls that distinguish between antisense gene inhibition and nonspecific biological effects of oligonucleotides. It is also preferred that these studies compare levels of the target protein with that of an internal control protein. Additionally, it is envisioned that results obtained using the antisense oligonucleotide are compared with those obtained using a control oligonucleotide. It is preferred that the control oligonucleotide is of approximately the same length as the test oligonucleotide and that the nucleotide sequence of the oligonucleotide differs from the antisense sequence no more than is necessary to prevent specific hybridization to the target sequence.

The antisense oligonucleotides can be DNA or RNA or chimeric mixtures or derivatives or modified versions thereof, single-stranded or double-stranded. The oligonucleotide can be modified at the base moiety, sugar moiety, or phosphate backbone, for example, to improve stability of the molecule. The oligonucleotide may include other appended groups such as peptides (e.g., for targeting host cell receptors in vivo), or agents facilitating transport across the cell membrane (see, e.g., Letsinger et al., 1989, Proc. Natl. Acad. Sci. U.S.A. 86:6553–6556; Lemaitre et al., 1987, Proc. Natl. Acad. Sci. 84:648–652; PCT Publication No. WO88/09810, published Dec. 15, 1988) or the blood-brain barrier (see, e.g., PCT Publication No. WO89/10134, published Apr. 25, 1988), hybridization-triggered cleavage agents. (See, e.g., Krol et al., 1988, *BioTechniques* 6:958–976) or intercalating agents. (See, e.g., Zon, 1988, Pharm. Res. 5:539–549). To this end, the oligonucleotide may be conjugated to another molecule, e.g., a peptide, hybridization triggered cross-linking agent, transport agent, hybridization-triggered cleavage agent, etc.

The antisense oligonucleotide may comprise at least one modified base moiety which is selected from the group including but not limited to 5-fluorouracil, 5-bromouracil, 5-chlorouracil, 5-iodouracil, hypoxanthine, xantine, 4-acetylcytosine, 5-(carboxyhydroxymethyl) uracil, 5-carboxymethylaminomethyl-2-thiouridine, 5-carboxymethylaminomethyluracil, dihydrouracil, beta-D-galactosylqueosine, inosine, N6-isopentenyladenine, 1-methylguanine, 1-methylinosine, 2,2-dimethylguanine, 2-methyladenine, 2-methylguanine, 3-methylcytosine, 5-methylcytosine, N6-adenine, 7-methylguanine, 5-methylaminomethyluracil, 5-methoxyaminomethyl-2-thiouracil, beta-D-mannosylqueosine, 5'-methoxycarboxymethyluracil, 5-methoxyuracil, 2-methylthio-N6-isopentenyladenine, uracil-5-oxyacetic acid (v), wybutoxosine, pseudouracil, queosine, 2-thiocytosine, 5-methyl-2-thiouracil, 2-thiouracil, 4-thiouracil, 5-methyluracil, uracil-5-oxyacetic acid methylester, uracil-5-oxyacetic acid (v), 5-methyl-2-thiouracil, 3-(3-amino-3-N-2-carboxypropyl) uracil, (acp3) w, and 2,6-diaminopurine.

The antisense oligonucleotide may also comprise at least one modified sugar moiety selected from the group including but not limited to arabinose, 2-fluoroarabinose, xylulose, and hexose.

In yet another embodiment, the antisense oligonucleotide comprises at least one modified phosphate backbone selected from the group consisting of a phosphorothioate, a phosphorodithioate, a phosphoramidothioate, a phosphoramidate, a phosphordiamidate, a methylphosphonate, an alkyl phosphotriester, and a formacetal or analog thereof.

In yet a further embodiment, the antisense oligonucleotide is an α-anomeric oligonucleotide. An α-anomeric oligonucleotide forms specific double-stranded hybrids with complementary RNA in which, contrary to the usual β-units, the strands run parallel to each other (Gautier et al., 1987, *Nucl. Acids Res.* 15:6625–6641). The oligonucleotide is a 2'-0-methylribonucleotide (Inoue et al., 1987, *Nucl. Acids Res.* 15:6131–6148), or a chimeric RNA-DNA analogue (Inoue et al., 1987, *FEBS Lett.* 215:327–330).

Oligonucleotides of the invention may be synthesized by standard methods known in the art, e.g. by use of an automated DNA synthesizer (such as are commercially available from Biosearch, Applied Biosystems, etc.). As examples, phosphorothioate oligonucleotides may be synthesized by the method of Stein et al. (1988, Nucl. Acids Res. 16:3209), methylphosphonate olgonucleotides can be prepared by use of controlled pore glass polymer supports (Sarin et al., 1988, Proc. Natl. Acad. Sci. U.S.A. 85:7448–7451), etc.

The antisense molecules should be delivered to cells containing an SR-BI promoter. A number of methods have been developed for delivering antisense DNA or RNA to cells; e.g., antisense molecules can be injected directly into the tissue site, or modified antisense molecules, designed to target the desired cells (e.g., antisense linked to peptides or antibodies that specifically bind receptors or antigens expressed on the target cell surface) can be administered systematically.

A preferred approach utilizes a recombinant DNA construct in which the antisense oligonucleotide is placed under the control of a strong pol III or pol II promoter. For example, a vector can be introduced in vivo such that it is taken up by a cell and directs the transcription of an antisense RNA. Such a vector can remain episomal or become chromosomally integrated, as long as it can be transcribed to produce the desired antisense RNA. Such vectors can be constructed by recombinant DNA technology methods standard in the art. Vectors can be plasmid, viral, or others known in the art, used for replication and expression in mammalian cells. Expression of the sequence encoding the antisense RNA can be by any promoter known in the art to act in mammalian, preferably human cells. Such promoters can be inducible or constitutive. Such promoters include but are not limited to: the SV40 early promoter region (Bernoist and Chambon, 1981, Nature 290:304–310), the promoter contained in the 3' long terminal repeat of Rous sarcoma virus (Yamamoto et al., 1980, Cell 22:787–797), the herpes thymidine kinase promoter (Wagner et al., 1981, Proc. Natl. Acad. Sci. U.S.A. 78:1441–1445), the regulatory sequences of the metallothionein gene (Brinster et al, 1982, Nature 296:39–42), etc. Any type of plasmid, cosmid, YAC or viral vector can be used to prepare the recombinant DNA construct which can be introduced directly into the tissue site; e.g., the choroid plexus or hypothalamus. Alternatively, viral vectors can be used which selectively infect the desired tissue; (e.g., for brain, herpes virus vectors may be used), in which case administration may be accomplished by another route (e.g., systematically). Vectors which can be used are further described above in the section entitled "Vectors".

Targeted homologous recombination can also be used to "knock out" the ability of an SR-BI promoter to initiate gene transcription (e.g., see Smithies et al., 1985, Nature 317:230–234; Thomas & Capecchi, 1987, Cell 51:503–512; Thompson et al., 1989 Cell 5:313–321; each of which is incorporated by reference herein in its entirety). For example, a completely unrelated DNA sequence flanked by DNA homologous to the endogenous SR-BI promoter can be used, with or without a selectable marker and/or a negative selectable marker, to transfect cells that contain the SR-BI promoter in vivo. Insertion of the DNA construct, via targeted homologous recombination, results in inactivation of the SR-BI promoter. Such approaches are particularly suited in non-human animals where modifications to ES (embryonic stem) cells can be used to generate animal offspring with an inactive SR-BI promoter (e.g., see Thomas & Capecchi 1987 and Thompson 1989, supra). However this approach can be adapted for use in humans provided the recombinant DNA constructs are directly administered or targeted to the required site in vivo using appropriate viral vectors, e.g., herpes virus vectors for delivery to brain tissue; e.g., the hypothalamus and/or choroid plexus.

Alternatively, gene expression from an SR-BI promoter can be reduced or suppressed by targeting deoxyribonucleotide sequences complementary to the SR-BI promoter to form triple helical structures that prevent transcription of the gene in target cells in the body. (See generally, Helene, C. 1991, Anticancer Drug Des., 6(6):569–84; Helene, C., et al., 1992, Ann, N.Y. Acad. Sci., 660:27–36; and Maher, L. J., 1992, Bioassays 14(12):807–15).

Nucleic acid molecules to be used in triple helix formation for the inhibition of transcription are preferably single stranded and composed of deoxyribonucleotides. The base composition of these oligonucleotides should promote triple helix formation via Hoogsteen base pairing rules, which generally require sizable stretches of either purines or pyrimidines to be present on one strand of a duplex. Nucleotide sequences may be pyrimidine-based, which will result in TAT and CGC triplets across the three associated strands of the resulting triple helix. The pyrimidine-rich molecules provide base complementarity to a purine-rich region of a single strand of the duplex in a parallel orientation to that strand. In addition, nucleic acid molecules may be chosen that are purine-rich, for example, containing a stretch of G residues. These molecules will form a triple helix with a DNA duplex that is rich in GC pairs, in which the majority of the purine residues are located on a single strand of the targeted duplex, resulting in CGC triplets across the three strands in the triplex.

Alternatively, the potential sequences that can be targeted for triple helix formation may be increased by creating a so called "switchback" nucleic acid molecule. Switchback molecules are synthesized in an alternating 5'–3', 3'–5' manner, such that they base pair with first one strand of a duplex and then the other, eliminating the necessity for a sizable stretch of either purines or pyrimidines to be present on one strand of a duplex.

Antisense RNA and DNA and triple helix molecules of the invention may be prepared by any method known in the art for the synthesis of DNA and RNA molecules. These include techniques for chemically synthesizing oligodeoxyribonucleotides and oligoribonucleotides well known in the art such as for example solid phase phosphoramidite chemical synthesis. Alternatively, RNA molecules may be generated by in vitro and in vivo transcription of DNA sequences encoding the antisense RNA molecule. Such DNA sequences may be incorporated into a wide variety of vectors which incorporate suitable RNA polymerase promoters such as the T7 or SP6 polymerase promoters. Alternatively, antisense cDNA constructs that synthesize antisense RNA constitutively or inducibly, depending on the promoter used, can be introduced stably into cell lines.

Moreover, various well-known modifications to nucleic acid molecules may be introduced as a means of increasing intracellular stability and half-life. Possible modifications include but are not limited to the addition of flanking sequences of ribonucleotides or deoxyribonucleotides to the 5' and/or 3' ends of the molecule or the use of phosphorothioate or 2' O-methyl rather than phosphodiesterase linkages within the oligodeoxyribonucleotide backbone.

4.3.4 Transcription Factors Binding to an SR-BI Promoter or Regulatory Element A promoter is typically bound by at least one transcription factor that mediates modulation of transcription from the promoter. Transcription factors bind specific regulatory elements. The human SR-BI nucleic acid sequence having SEQ ID NO: 1 has been analyzed using a computer program (TF Search based on TFMATRIX transcription factor binding site profile database by E. Wingeneder, R. Knueppel, P. Dietze, and H. Karas (GBF-Braunschweig)(http://www.genome.ad.jp/sit/tfsearchhtm1)) for such sites and numerous transcription factor binding sites have been identified. The result of the search is shown in Table I. It is likely that other transcription factors than those cited in the TF Search bind to the SR-BI promoter, including as yet unknown transcription factors. Such transcription factors, as well as nucleic acids encoding such transcription factors and the binding sites to which they bind are also within the scope of the invention. Furthermore, additional transcription factor binding sites are likely to be present in the 7 kb nucleic acid deposited with the ATCC on Mar. 5, 1997, and having ATCC Deposit No. 97907.

Various methods can be used to characterize and isolate such transcription factors. Some of the most useful methods are described in the Example section. The availability of purified or recombinant transcription factors that bind regulatory elements in an SR-BI gene will allow the use of high throughput assays for isolating compounds which modulate binding of these factors to the regulatory element, resulting in modulation of the SR-BI gene transcription. Assays that can be used are further described in the Examples.

The availability of nucleic acids encoding transcription factors modulating the expression of SR-BI genes will also allow for methods for modulating the expression of this gene by increasing or decreasing the amount of such transcription factors in cells. Modulating the protein level of a transcription factor can be achieved by using specific compounds or by introducing into the cell expression constructs driving the expression of the transcription factor or producing antisense molecules blocking the expression of the transcription factor.

Alternatively, compounds modulating the binding of transcription factors to an SR-BI promoter region can be identified in assays which do not require an isolated transcription factor. For example, EMSA assays can be performed. According to this assay, which is further described in the Examples, a cellular or nuclear extract is prepared from a cell in which the SR-BI gene is expressed, and the extract is incubated in the presence of a nucleic acid comprising at least one trancription factor binding site. Compounds, e.g., competing nucleic acids (for example, yeast tRNA) can be added to reduce or eliminate non specific binding of proteins to the nucleic acid. After incubation for an adequate amount of time, e.g., 20 minutes, the mixture of nucleic acid and protein is then subjected to gel electophoresis allowing for the separation of complexes between nucleic acid and proteins and non complexed nucleic acids and proteins. In a preferred embodiment, the nucleic acid is radioactively labeled and the protein-DNA complex is detected by autoradiography of the gel.

Specific binding of a protein to the nucleic acid can be confirmed by performing competition experiments, e.g., with irrelevant nucleic acids or non labeled nucleic acids having the same nucleic acid sequence as the labeled nucleic acid, and non labeled mutated forms of the labeled nucleic acid. Thus, if binding of a protein to the nucleic acid is competed by an irrelevant nucleic acid, the binding is non specific. Alternatively, if binding of a protein to the nucleic acid is not competed away by an irrelevant nucleic acid, the binding is specific.

Furthermore, the specific nucleotides of the nucleic acid that are involved in binding with the protein can be identified by performing competition experiments, for example, using mutated forms of the labeled nucleic acid. Accordingly, if a nucleic acid which differs from the labeled nucleic acid by one nucleotide, is not capable of competing away binding of the protein to the labeled nucleic acid, the nucleotide that has been mutated is important in binding of the transcription factor to the nucleic acid. Thus, by preparing nucleic acids having various mutated nucleotides, it is possible to determine which nucleotides are important for binding of a transcription factor to this nucleic acid.

It is also possible to identify the transcription factor that is binding to a certain nucleic acid, as observed in EMSA. In fact, it is possible to add antibodies that bind specifically to individual transcription factors in EMSA assays. If the transcription factor is indeed recognized by an antibody in the EMSA assay, the protein-DNA complex that was seen in the absence of the antibody will be absent, or located at a differing position after the EMSA. Thus, it is possible to identify transcription factors binding to an SR-BI promoter by, e.g., performing EMSA assays including antibodies which specifically bind to transcription factors identified using a promoter analysis program, e.g, GRAIL.

Additional methods can be used to identify and/or isolate transcription factors binding to an SR-BI promoter or regulatory element thereof. For example, known transcription factors can be produced recombinantly and binding of these factors to the SR-BI nucleic acid can be tested. For example, the transcription factors having binding sites identified by the GRAIL analysis can be produced recombinantly, or obtained from a commercial source, and binding of these to an SR-BI promoter or regulatory element can be tested, e.g., in gel retardation assays, similar to those described above and in the Examples. Briefly, a recombinant or purified transcription factor is incubated with a labeled nucleic acid of choice in the presence of an adequate buffer and reagents that inhibit nonspecific binding of the protein to the nucleic acid, and the reaction can then be subjected to a separation, e.g., by gel electrophoresis. The presence of a retarded complex observed on the autoradiography of the gel which is absent in a reaction that does not contain the recombinant or purified protein indicates binding of the transcription factor to the SR-BI promoter or regulatory element present in the nucleic acid used as a probe.

In another method for identifying transcription factor binding to an SR-BI promoter or regulatory element thereof, a foot-printing experiment is performed on the specific nucleic acid. Accordingly, a nucleic acid containing an SR-BI promoter or at least one regulatory element thereof is labeled and incubated with a nuclear extract from a cell expressing the SR-BI receptor. The reaction is then incubated with a reagent which cuts the nucleic acid, (e.g., Dnase) and the fragments are separated by electrophoresis. Following autoradiography of the gel, the comparison of the pattern of fragments obtained from a reaction incubated with and without protein reveals the portions of the nucleic acid which are bound by the protein. This experiment can also be performed with purified or recombinant proteins. DNAse I footprinting can also be performed slightly differently using PCR, as described, e.g., in "PCR Protocols: A Guide to Methods and Applications", Ed. Michael E. Innis, David H. Gelfand, John Sninsky, and Thomas J. White, Academic Press.

In yet another method, the binding site of a transcription factor is identified using a methylation or ethylation interference assay. In these methods, a nucleic acid comprising an SR-BI promoter or at least one regulatory element thereof is labeled and incubated with an agent which modifies certain bases of the nucleic acid, such as an agent which methylates specific bases. The modified nucleic acid is then incubated with a nuclear extract or purified protein or recombinant protein and the reaction is subjected to electrophoresis. A comparison of the pattern of binding of a nucleic acid incubated with or without protein will reveal where the protein binds.

Other experiments allow the characterization of a promoter or regulatory element in vivo. For example, the location of regions of a 5' flanking region of a gene which are involved in transcription can be identified by identifying Dnase I hypersensitive sites in the nucleic acid. These regions are located in open chromatin, accessible to the Dnase I, and thus reflect active chromatin. In yet another assay, it is possible to determine in vivo the sequences that are bound by transcription factors. For example, the techniques of Ligated Mediated PCR (LMPC) can be used for that purpose. In this technique, dimethylsulfate (DMS) is added to cells expressing SR-BI. This reagent will methylate the chromosomal DNA. The DNA is then treated with piperidine, which cuts it next to the modified nucleotides. Accordingly, nucleic acid regions bound by protein will be protected from the methylating agent and will not be cut by piperidine.

A transcription factor binding to an SR-BI promoter or regulatory element thereof can be isolated by any of numerous techniques, such as those described below and in the Examples. For example, a transcription factor can be isolated using the technique of λgt11 phage expression library. According to this method, a λgt11 expression library, prepared from cells expressing SR-BI is screened with a labeled nucleic acid comprising an SR-BI promoter or at least one regulatory element thereof.

A protein binding to an SR-BI promoter can also be isolated and cloned using methods of purification of the protein on columns, such as affinity columns having the nucleic acid of interest, and sequencing of the N-terminal portion of the protein. Degenerate oligonucleotides corresponding to the amino acid sequence determined can then be used to clone the gene encoding the isolated protein.

Yet another system that can be used to isolate a transcription factor is the yeast 1- hybrid system and systems deriving therefrom, such as a system performed in a mammalian cell. This system is further described in Example 5.8.

Furthermore, various techniques exist for isolating and/or cloning a protein interacting with another protein. One example of such a system is the yeast 2-hybrid system. Accordingly, such a system could be used to isolate and clone proteins interacting with transcription factors binding an SR-BI promoter or regulatory element thereof.

Once a protein has been identified as binding to an SR-BI promoter or regulatory element thereof, it can be determined whether this protein affects SR-BI transcription in a positive or in a negative manner. The nucleic acid encoding the newly isolated protein can be cotransfected into cells together with a reporter construct under the control of the SR-BI promoter or regulatory element thereof. Expression of the reporter construct indicates that the protein is a positive transcription factor. Alternatively, if the basic level of transcription from the promoter is reduced upon expression of the newly isolated protein, then this protein acts negatively on transcription. The transcription factor may also be active only upon a modification, which can, e.g., occur upon treatment of the cell with a specific drug. This can be determined by testing various drugs. For example, the SR-BI nucleic acid sa-12 contains a GATA-1 response element which may be responsive to estrogen.

Thus, the invention provides various methods for identifying and cloning transcription factors involved in regulating expression from an SR-BI promoter. However, as is detailed below, it is not necessary to have identified such transcription factors in order to identify drugs which modulate SR-BI promoter activity.

4.4. Drug Screening Assays and Transgenic Animals

4.4.1 Cell Based and Cell-free Assays

The invention provides method for treating a subject having a disorder or condition associated with aberrant SR-BI activity, e.g., SR-BI expression. In one embodiment of the invention, the treatment of the subject consists of administering to the subject a compound which modulates SR-BI expression. The following section describes various methods that can be used for isolating such compounds.

In many drug screening programs which test libraries of compounds and natural extracts, high throughput assays are desirable in order to maximize the number of compounds surveyed in a given period of time. Assays which are performed in cell-free systems, such as may be derived with purified or semi-purified proteins, are often preferred as "primary" screens in that they can be generated to permit rapid development and relatively easy detection of an alteration in a molecular target which is mediated by a test compound. Moreover, the effects of cellular toxicity and/or bioavailability of the test compound can be generally ignored in the in vitro system, the assay instead being focused primarily on the effect of the drug on the molecular target as may be manifest in an alteration of binding affinity with upstream or downstream elements.

In one embodiment of the invention, a compound, e.g., a small molecule, can be identified by performing assays in which an SR-BI promoter binding partner is incubated with a nucleic acid comprising an SR-BI promoter or regulatory element thereof and the effect of a test compound on the specific binding of the SR-BI promoter binding partner to the nucleic acid is determined. The SR-BI promoter binding partner can be, for example, a nuclear extract prepared from a cell expressing SR-BI. Alternatively, the SR-BI promoter binding partner can be an isolated, purified or cloned transcription factor. Modulation of binding to the nucleic acid can be determined, e.g., in an EMSA assay, such as those described above. Thus, a test compound can be incubated together with a DNA, which is preferably labeled, comprising an SR-BI promoter or regulatory element thereof, and the SR-BI promoter binding partner. The reaction mixture is then subjected to an electrophoresis and the amount of "retarded" protein-DNA complex is compared to the amount of retarded complex from a binding reaction in which the test compound has not been added. A lower level of complex observed in the reaction that contains the test compound compared to the level of complex observed in the reaction that does not contain the test compound indicates that the test compound inhibits or reduces binding of one or more SR-BI promoter binding partners to the SR-BI promoter or regulatory element thereof.

This type of reaction can be performed in high throughput type of assays. For example, it is possible to attach the SR-BI promoter binding partner to 96 well plates, add labeled nucleic acid and a test compound. After the binding reaction, and washing of the plates to remove non specific binding, it is then possible to "read" the amount of label present in each well.

In another embodiment, the effect of a test compound on binding of an SR-BI promoter binding partner (e.g., transcription factor) to an SR-BI promoter or regulatory element thereof is measured using any of the assays described in the previous section.

Several in vivo methods can also be used to identify compounds that modulate an SR-BI activity. In one embodiment, the invention provides a method comprising incubating a cell expressing SR-BI with a test compound and measuring the SR-BI mRNA or protein level. SR-BI mRNA levels can be determined by Northern blot hybridization as described in the Examples. SR-BI mRNA levels can also be determined by methods involving PCR. Other sensitive methods for measuring mRNA, which can be used in high throughput assays, e.g., a method using a DELFIA endpoint detection and quantification method, are described, e.g., in Webb and Hurskainen (1996) *Journal of Biomolecular Screening* 1:119. SR-BI protein levels can be determined by immunoprecipitations or immunohistochemistry using an antibody that specifically recognizes SR-BI. Such an antibody is described, e.g,. In Acton et al. (1996) Science 271:518.

The invention further provides for another in vivo assay for identifying compounds which modulate SR-BI activity. For example, a reporter construct can be constructed in which a reporter gene is under the control of an SR-BI nucleic acid comprising a promoter or at least one regulatory element thereof. In one embodiment the SR-BI nucleic acid comprises the nucleic acid shown as SEQ ID NO: 1. In yet another embodiment, the SR-BI nucleic acid comprises at least about 6 consecutive nucleotides from SEQ ID NO: 1 or homolog thereof. In other preferred embodiments of the invention, the SR-BI nucleic acid comprises at least about 10, at least about 15, at least about 20, or at least about 25 consecutive nucleotides from SEQ ID NO: 1 or homolog thereof. The SR-BI nucleic acid can also be chosen to contain one or more of the transcription factor binding sites listed in Table I.

The reporter gene can be any gene encoding a protein which can readily be detected. The reporter gene is preferably a gene encoding luciferase. According to the method of the invention, cells are transfected with the reporter construct comprising an SR-BI promoter or at least one regulatory element thereof. Transfection can be transient or stable. It is also possible to transfect a cell with more than one reporter construct. The transfected cells can then be incubated in the presence or absence of a test compound for an appropriate amount of time and the level of expression of the reporter gene can be determined. Compounds which produce a statistically significant change in expression of the reporter gene (either suppression indicating that the test compound is an antagonist of SR-BI initiated gene expression or potentiation indicating that the test compound is an agonist of SR-BI initiated gene expression) can be identified (See e.g, in the Examples).

Similar assays can also be performed using a cell or nuclear extract instead of cells. Thus, in one embodiment, the invention provides a method for identifying a compound which modulates SR-BI activity, comprising incubating a reporter construct comprising an SR-BI promoter or at least one regulatory element thereof with a nuclear or cellular extract, or isolated nuclei, in the presence or absence of test compound. Expression of the test compound is then measured, e.g., by including a labeled nucleotide in the reaction and measuring the amount of label incorporated in the product transcribed from the reporter construct. Other methods can also be used to determine the amount of reporter gene expression in this system, such as the measure of the amount of protein encoded by the reporter gene.

It is preferable to use cells expressing SR-BI for use in the transfection assays described above. Exemplary cell lines include liver cell lines such as HepG2; as well as other generic mammalian cell lines which express SR-BI. Further, the transgenic animals discussed herein may be used to generate cell lines, containing one or more cell types involved, for example, in cardiovascular disease, that can be used as cell culture models for this disorder. While primary cultures derived from the cardiovascular disease transgenic animals of the invention may be utilized, the generation of continuous cell lines is preferred. For examples of techniques which may be used to derive a continuous cell line from the transgenic animals, see Small et al., (1985) *Mol. Cell Biol.* 5:642–648.

Monitoring the influence of compounds on cells may be applied not only in basic drug screening, but also in clinical trials. In such clinical trials, the expression of a panel of genes may be used as a "read out" of a particular drug's therapeutic effect.

4.4.2 Animal-based Systems

In yet another embodiment of the invention, compounds that modulate SR-BI activity in vivo can be identified in non-human animals. In one embodiment of the invention, a non-human animal, e.g., a mouse, is treated with a compound, such as a compound identified in one of the assays described above. After an appropriate amount of time, the level of SR-BI activity is determined and compared to its activity in a mouse which has not received the test compound. SR-BI activity in the mouse can be determined by various methods, e.g., by determining mRNA levels, by Northern blot hybridization, or by in situ hybridization. Alternatively, SR-BI activity can be determined by measuring SR-BI protein levels, e.g., by immunohistochemistry.

To identify a compound which modulates an SR-BI promoter or regulatory element thereof, where the SR-BI promoter or regulatory element is from the human species, the invention provides a method using transgenic non-human mammals. The transgenic animals comprise cells (of that animal) which contain a transgene of the present invention and which preferably (though optionally) express an exogenous SR-BI promoter in one or more cells in the animal. The transgene preferably contains an SR-BI promoter or at least one regulatory element thereof and is preferably of human origin. A preferred nucleic acid is a nucleic acid having SEQ ID NO: 1, a fragment thereof or homolog thereof, as well as complements thereto. An SR-BI promoter transgene can be wildtype or mutant. The promoter or at least one regulatory element is preferably operably linked to a reporter gene. In a preferred embodiment, the reporter gene encodes a protein which can readily be detected, e.g, by a colorimetric assay. A preferred reporter gene is the bacterial beta-galactosidase gene encoded by the lacZ gene.

In preferred embodiments, the expression of the transgene is restricted to specific subsets of cells, tissues or developmental stages utilizing, for example, cis-acting sequences that control expression in the desired pattern. In the present invention, such mosaic expression of an SR-BI promoter can be essential for many forms of lineage analysis and can additionally provide a means to assess the effects of, for example, the absence of a functional SR-BI promoter which might grossly alter development in small patches of tissue within an otherwise normal embryo. Temporal patterns of expression can be provided by, for example, conditional recombination systems or prokaryotic transcriptional regulatory sequences.

Genetic techniques which allow for the expression of transgenes, which can be regulated via site-specific genetic manipulation in vivo are known to those skilled in the art. For instance, genetic systems are available which allow for the regulated expression of a recombinase that catalyzes the genetic recombination a target sequence. As used herein, the phrase "target sequence" refers to a nucleotide sequence that is genetically recombined by a recombinase. The target sequence is flanked by recombinase recognition sequences and is generally either excised or inverted in cells expressing recombinase activity. Recombinase catalyzed recombination events can be designed such that recombination of the target sequence results in either the activation or suppression of expression by one of the subject SR-BI promoters. For example, excision of a target sequence which interferes with the expression of a recombinant gene, such as one which encodes an antagonistic homolog or an antisense transcript, can be designed to activate expression of that gene. This interference with expression of the protein can result from a variety of mechanisms, such as spatial separation of the gene from the promoter element or an internal stop codon. Moreover, the transgene can be made wherein the coding sequence of the gene is flanked by recombinase recognition sequences and is initially transfected into cells in a 3' to 5' orientation with respect to the promoter element. In such an instance, inversion of the target sequence will reorient the subject gene by placing the 5' end of the coding sequence in an orientation with respect to the promoter element which allow for promoter driven transcriptional activation.

The transgenic animals of the present invention all include within a plurality of their cells a transgene of the present invention. Since it is possible to produce transgenic organisms of the invention utilizing one or more of the transgene constructs described herein, a general description will be given of the production of transgenic organisms by referring generally to exogenous genetic material. This general description can be adapted by those skilled in the art in order to incorporate specific transgene sequences into organisms utilizing the methods and materials described below.

In an illustrative embodiment, either the cre/loxP recombinase system of bacteriophage P1 (Lakso et al. (1992) PNAS 89:6232–6236; Orban et al. (1992) PNAS 89:6861–6865) or the FLP recombinase system of Saccharomyces cerevisiae (O'Gorman et al. (1991) Science 251:1351–1355; PCT publication WO 92/15694) can be used to generate in vivo site-specific genetic recombination systems. Cre recombinase catalyzes the site-specific recombination of an intervening target sequence located between loxP sequences. loxP sequences are 34 base pair nucleotide repeat sequences to which the Cre recombinase binds and are required for Cre recombinase mediated genetic recombination. The orientation of loxP sequences determines whether the intervening target sequence is excised or inverted when Cre recombinase is present (Abremski et al. (1984) J. Biol. Chem. 259:1509–1514); catalyzing the excision of the target sequence when the loxP sequences are oriented as direct repeats and catalyzes inversion of the target sequence when loxP sequences are oriented as inverted repeats.

Accordingly, genetic recombination of the target sequence is dependent on expression of the Cre recombinase. Expression of the recombinase can be regulated by promoter elements which are subject to regulatory control, e.g., tissue-specific, developmental stage-specific, inducible or repressible by externally added agents. This regulated control will result in genetic recombination of the target sequence only in cells where recombinase expression is mediated by the promoter element. Thus, the activation expression of a recombinant protein can be regulated via control of recombinase expression.

Use of the cre/loxP recombinase system to regulate expression of a recombinant protein requires the construction of a transgenic animal containing transgenes encoding both the Cre recombinase and the subject protein. Animals containing both the Cre recombinase and a recombinant gene can be provided through the construction of "double" transgenic animals. A convenient method for providing such animals is to mate two transgenic animals each containing a transgene, e.g., a gene and recombinase gene.

One advantage derived from initially constructing transgenic animals containing a transgene in a recombinase-mediated expressible format derives from the likelihood that the subject protein, whether agonistic or antagonistic, can be deleterious upon expression in the transgenic animal. In such an instance, a founder population, in which the subject transgene is silent in all tissues, can be propagated and maintained. Individuals of this founder population can be crossed with animals expressing the recombinase in, for example, one or more tissues and/or a desired temporal pattern. Thus, the creation of a founder population in which, for example, an antagonistic transgene is silent will allow the study of progeny from that founder in which disruption of mediated induction in a particular tissue or at certain developmental stages would result in, for example, a lethal phenotype.

Similar conditional transgenes can be provided using prokaryotic promoter sequences which require prokaryotic proteins to be simultaneous expressed in order to facilitate expression of the transgene. Exemplary promoters and the corresponding trans-activating prokaryotic proteins are given in U.S. Pat. No. 4,833,080.

Moreover, expression of the conditional transgenes can be induced by gene therapy-like methods wherein a gene encoding the trans-activating protein, e.g. a recombinase or a prokaryotic protein, is delivered to the tissue and caused to be expressed, such as in a cell-type specific manner. By this method, a transgene could remain silent into adulthood until "turned on" by the introduction of the trans-activator.

In an exemplary embodiment, the "transgenic non-human animals" of the invention are produced by introducing transgenes into the germline of the non-human animal. Embryonal target cells at various developmental stages can be used to introduce transgenes. Different methods are used depending on the stage of development of the embryonal target cell. The specific line(s) of any animal used to practice this invention are selected for general good health, good embryo yields, good pronuclear visibility in the embryo, and good reproductive fitness. In addition, the haplotype is a significant factor. For example, when transgenic mice are to be produced, strains such as C57BL/6 or FVB lines are often used (Jackson Laboratory, Bar Harbor, Me.). Preferred strains are those with H-$2^b$, H-$2^d$ or H-2q haplotypes such as C57BL/6 or DBA/1. The line(s) used to practice this invention may themselves be transgenics, and/or may be knockouts (i.e., obtained from animals which have one or more genes partially or completely suppressed).

In one embodiment, the transgene construct is introduced into a single stage embryo. The zygote is the best target for micro-injection. In the mouse, the male pronucleus reaches the size of approximately 20 micrometers in diameter which allows reproducible injection of 1–2pl of DNA solution. The use of zygotes as a target for gene transfer has a major advantage in that in most cases the injected DNA will be incorporated into the host gene before the first cleavage (Brinster et al. (1985) *PNAS* 82:4438–4442). As a consequence, all cells of the transgenic animal will carry the incorporated transgene. This will in general also be reflected in the efficient transmission of the transgene to offspring of the founder since 50% of the germ cells will harbor the transgene.

Normally, fertilized embryos are incubated in suitable media until the pronuclei appear. At about this time, the nucleotide sequence comprising the transgene is introduced into the female or male pronucleus as described below. In some species such as mice, the male pronucleus is preferred. It is most preferred that the exogenous genetic material be added to the male DNA complement of the zygote prior to its being processed by the ovum nucleus or the zygote female pronucleus. It is thought that the ovum nucleus or female pronucleus release molecules which affect the male DNA complement, perhaps by replacing the protamines of the male DNA with histones, thereby facilitating the combination of the female and male DNA complements to form the diploid zygote.

Thus, it is preferred that the exogenous genetic material be added to the male complement of DNA or any other complement of DNA prior to its being affected by the female pronucleus. For example, the exogenous genetic material is added to the early male pronucleus, as soon as possible after the formation of the male pronucleus, which is when the male and female pronuclei are well separated and both are located close to the cell membrane. Alternatively, the exogenous genetic material could be added to the nucleus of the sperm after it has been induced to undergo decondensation. Sperm containing the exogenous genetic material can then be added to the ovum or the decondensed sperm could be added to the ovum with the transgene constructs being added as soon as possible thereafter.

Introduction of the transgene nucleotide sequence into the embryo may be accomplished by any means known in the art such as, for example, microinjection, electroporation, or lipofection. Following introduction of the transgene nucleotide sequence into the embryo, the embryo may be incubated in vitro for varying amounts of time, or reimplanted into the surrogate host, or both. In vitro incubation to maturity is within the scope of this invention. One common method is to incubate the embryos in vitro for about 1–7 days, depending on the species, and then reimplant them into the surrogate host.

For the purposes of this invention, a zygote is essentially the formation of a diploid cell which is capable of developing into a complete organism. Generally, the zygote will be comprised of an egg containing a nucleus formed, either naturally or artificially, by the fusion of two haploid nuclei from a gamete or gametes. Thus, the gamete nuclei must be ones which are naturally compatible, i.e., ones which result in a viable zygote capable of undergoing differentiation and developing into a functioning organism. Generally, a euploid zygote is preferred. If an aneuploid zygote is obtained, then the number of chromosomes should not vary by more than one with respect to the euploid number of the organism from which either gamete originated.

In addition to similar biological considerations, physical ones also govern the amount (e.g., volume) of exogenous genetic material which can be added to the nucleus of the zygote or to the genetic material which forms a part of the zygote nucleus. If no genetic material is removed, then the amount of exogenous genetic material which can be added is limited by the amount which will be absorbed without being physically disruptive. Generally, the volume of exogenous genetic material inserted will not exceed about 10 picoliters. The physical effects of addition must not be so great as to physically destroy the viability of the zygote. The biological limit of the number and variety of DNA sequences will vary depending upon the particular zygote and functions of the exogenous genetic material and will be readily apparent to one skilled in the art, because the genetic material, including the exogenous genetic material, of the resulting zygote must be biologically capable of initiating and maintaining the differentiation and development of the zygote into a functional organism.

The number of copies of the transgene constructs which are added to the zygote is dependent upon the total amount of exogenous genetic material added and will be the amount which enables the genetic transformation to occur. Theoretically only one copy is required; however, generally, numerous copies are utilized, for example, 1,000–20,000 copies of the transgene construct, in order to insure that one copy is functional. As regards the present invention, there will often be an advantage to having more than one functioning copy of each of the inserted exogenous DNA sequences to enhance the phenotypic expression of the exogenous DNA sequences.

Any technique which allows for the addition of the exogenous genetic material into nucleic genetic material can be utilized so long as it is not destructive to the cell, nuclear membrane or other existing cellular or genetic structures. The exogenous genetic material is preferentially inserted into the nucleic genetic material by microinjection. Microinjection of cells and cellular structures is known and is used in the art.

Reimplantation is accomplished using standard methods. Usually, the surrogate host is anesthetized, and the embryos are inserted into the oviduct. The number of embryos implanted into a particular host will vary by species, but will usually be comparable to the number of off spring the species naturally produces.

Transgenic offspring of the surrogate host may be screened for the presence and/or expression of the transgene by any suitable method. Screening is often accomplished by Southern blot or Northern blot analysis, using a probe that is complementary to at least a portion of the transgene. Western blot analysis using an antibody against the protein encoded by the transgene may be employed as an alternative or additional method for screening for the presence of the transgene product. Typically, DNA is prepared from tail tissue and analyzed by Southern analysis or PCR for the transgene. Alternatively, the tissues or cells believed to express the transgene at the highest levels are tested for the presence and expression of the transgene using Southern analysis or PCR, although any tissues or cell types may be used for this analysis.

Alternative or additional methods for evaluating the presence of the transgene include, without limitation, suitable biochemical assays such as enzyme and/or immunological assays, histological stains for particular marker or enzyme activities, flow cytometric analysis, and the like. Analysis of the blood may also be useful to detect the presence of the transgene product in the blood, as well as to evaluate the effect of the transgene on the levels of various types of blood cells and other blood constituents.

Progeny of the transgenic animals may be obtained by mating the transgenic animal with a suitable partner, or by in vitro fertilization of eggs and/or sperm obtained from the transgenic animal. Where mating with a partner is to be performed, the partner may or may not be transgenic and/or a knockout; where it is transgenic, it may contain the same or a different transgene, or both. Alternatively, the partner may be a parental line. Where in vitro fertilization is used, the fertilized embryo may be implanted into a surrogate host or incubated in vitro, or both. Using either method, the progeny may be evaluated for the presence of the transgene using methods described above, or other appropriate methods.

The transgenic animals produced in accordance with the present invention will include exogenous genetic material. As set out above, the exogenous genetic material will, in certain embodiments, be a DNA sequence which results in the production of a protein (either agonistic, antagonistic or a reporter protein), antisense transcript, or a mutant protein. Further, in such embodiments the sequence is linked to an SR-BI promoter or regulatory elementmoter fragment, or modified form thereof.

Transgenic animals of the invention can be used to identify functional promoter elements of an SR-BI promoter. In one embodiment, transgenic animals are prepared which contain a reporter gene under the control of different SR-BI promoter fragments or modifications thereof. The level of expression of the reporter construct is then measured in various tissues. These transgenic mice can be used to identify regions of the promoter involved in tissue specific expression of SR-BI, by, e.g., determining the level of expression of the reporter gene in various tissues. These transgenic mice can also be used to identify regions of the SR-BI promoter which have inducible elements.

Transgenic animals of the invention can also be used to identify compounds which modulate transcription from an SR-BI promoter. Accordingly, an animal transgenic for a reporter construct under the control of an SR-BI promoter, fragment thereof, or modified form thereof is treated with compounds, e.g., small molecules, and the level of expression of the transgene is determined in different tissues. Such assays are further described in the Examples. These in vivo assays are particularly useful to confirm the effect of a compound which has been shown in in vitro assays to affect transcription from an SR-BI promoter.

Retroviral infection can also be used to introduce transgene into a non-human animal. The developing non-human embryo can be cultured in vitro to the blastocyst stage. During this time, the blastomeres can be targets for retroviral infection (Jaenich, R. (1976) *PNAS* 73:1260–1264). Efficient infection of the blastomeres is obtained by enzymatic treatment to remove the zona pellucida (*Manipulating the Mouse Embryo,* Hogan eds. (Cold Spring Harbor Laboratory Press, Cold Spring Harbor, 1986). The viral vector system used to introduce the transgene is typically a replication-defective retrovirus carrying the transgene (Jahner et al. (1985) *PNAS* 82:6927–6931; Van der Putten et al. (1985) *PNAS* 82:6148–6152). Transfection is easily and efficiently obtained by culturing the blastomeres on a monolayer of virus-producing cells (Van der Putten, supra; Stewart et al. (1987) *EMBO J.* 6:383–388). Alternatively, infection can be performed at a later stage. Virus or virus-producing cells can be injected into the blastocoele (Jahner et al. (1982) *Nature* 298:623–628). Most of the founders will be mosaic for the transgene since incorporation occurs only in a subset of the cells which formed the transgenic non-human animal. Further, the founder may contain various retroviral insertions of the transgene at different positions in the genome which generally will segregate in the offspring. In addition, it is also possible to introduce transgenes into the germ line by intrauterine retroviral infection of the midgestation embryo (Jahner et al. (1982) supra).

A third type of target cell for transgene introduction is the embryonal stem cell (ES). ES cells are obtained from pre-implantation embryos cultured in vitro and fused with embryos (Evans et al. (1981) *Nature* 292:154–156; Bradley et al. (1984) *Nature* 309:255–258; Gossler et al. (1986) *PNAS* 83: 9065–9069; and Robertson et al. (1986) *Nature* 322:445–448). Transgenes can be efficiently introduced into the ES cells by DNA transfection or by retrovirus-mediated transduction. Such transformed ES cells can thereafter be combined with blastocysts from a non-human animal. The ES cells thereafter colonize the embryo and contribute to the germ line of the resulting chimeric animal. For review see Jaenisch, R. (1988) *Science* 240:1468–1474.

In one embodiment, gene targeting, which is a method of using homologous recombination to modify an animal's genome, can be used to introduce changes into cultured embryonic stem cells. By targeting a gene of interest in ES cells, these changes can be introduced into the germlines of animals to generate chimeras. The gene targeting procedure is accomplished by introducing into tissue culture cells a DNA targeting construct that includes a segment homologous to a target locus, and which also includes an intended sequence modification to the genomic sequence (e.g., insertion, deletion, point mutation). The treated cells are then screened for accurate targeting to identify and isolate those which have been properly targeted.

Gene targeting in embryonic stem cells is in fact a scheme contemplated by the present invention as a means for disrupting a gene function through the use of a targeting transgene construct designed to undergo homologous recombination with one or more genomic sequences. The targeting construct can be arranged so that, upon recombination with an element of a gene, a positive selection marker is inserted into (or replaces) coding sequences of the targeted gene. The inserted sequence functionally disrupts the gene, while also providing a positive selection trait. Exemplary targeting constructs are described in more detail below.

Generally, the embryonic stem cells (ES cells) used to produce the knockout animals will be of the same species as the knockout animal to be generated. Thus for example, mouse embryonic stem cells will usually be used for generation of knockout mice.

Embryonic stem cells are generated and maintained using methods well known to the skilled artisan such as those described by Doetschman et al. (1985) *J. Embryol. Exp. Morphol.* 87:27–45). Any line of ES cells can be used, however, the line chosen is typically selected for the ability of the cells to integrate into and become part of the germ line of a developing embryo so as to create germ line transmission of the knockout construct. Thus, any ES cell line that is believed to have this capability is suitable for use herein. One mouse strain that is typically used for production of ES cells, is the 129J strain. Another ES cell line is murine cell line D3 (American Type Culture Collection, catalog no. CKL 1934) Still another preferred ES cell line is the WW6 cell line (Ioffe et al. (1995) *PNAS* 92:7357–7361). The cells are cultured and prepared for knockout construct insertion using methods well known to the skilled artisan, such as those set forth by Robertson in: Teratocarcinomas and Embryonic Stem Cells: A Practical Approach, E. J. Robertson, ed. IRL Press, Washington, D.C. [1987]); by Bradley et al. (1986) *Current Topics in Devel. Biol.* 20:357–371); and by Hogan et al. (Manipulating the Mouse Embryo: A Laboratory Manual, Cold Spring Harbor Laboratory Press, Cold Spring Harbor, N.Y. [1986]).

Insertion of the knockout construct into the ES cells can be accomplished using a variety of methods well known in the art including for example, electroporation, microinjection, and calcium phosphate treatment. A preferred method of insertion is electroporation.

Each knockout construct to be inserted into the cell must first be in the linear form. Therefore, if the knockout construct has been inserted into a vector (described infra), linearization is accomplished by digesting the DNA with a suitable restriction endonuclease selected to cut only within the vector sequence and not within the knockout construct sequence.

For insertion, the knockout construct is added to the ES cells under appropriate conditions for the insertion method chosen, as is known to the skilled artisan. Where more than one construct is to be introduced into the ES cell, each knockout construct can be introduced simultaneously or one at a time.

If the ES cells are to be electroporated, the ES cells and knockout construct DNA are exposed to an electric pulse using an electroporation machine and following the manufacturer's guidelines for use. After electroporation, the ES cells are typically allowed to recover under suitable incubation conditions. The cells are then screened for the presence of the knockout construct.

Screening can be accomplished using a variety of methods. Where the marker gene is an antibiotic resistance gene, for example, the ES cells may be cultured in the presence of an otherwise lethal concentration of antibiotic. Those ES cells that survive have presumably integrated the knockout construct. If the marker gene is other than an antibiotic resistance gene, a Southern blot of the ES cell genomic DNA can be probed with a sequence of DNA designed to hybridize only to the marker sequence Alternatively, PCR can be used. Finally, if the marker gene is a gene that encodes an enzyme whose activity can be detected (e.g., b-galactosidase), the enzyme substrate can be added to the cells under suitable conditions, and the enzymatic activity can be analyzed. One skilled in the art will be familiar with other useful markers and the means for detecting their presence in a given cell. All such markers are contemplated as being included within the scope of the teaching of this invention.

The knockout construct may integrate into several locations in the ES cell genome, and may integrate into a different location in each ES cell's genome due to the occurrence of random insertion events. The desired location of insertion is in a complementary position to the DNA sequence to be knocked out, e.g., the coding sequence, transcriptional regulatory sequence, etc. Typically, less than about 1–5% of the ES cells that take up the knockout construct will actually integrate the knockout construct in the desired location. To identify those ES cells with proper integration of the knockout construct, total DNA can be extracted from the ES cells using standard methods. The DNA can then be probed on a Southern blot with a probe or probes designed to hybridize in a specific pattern to genomic DNA digested with particular restriction enzyme(s). Alternatively, or additionally, the genomic DNA can be amplified by PCR with probes specifically designed to amplify DNA fragments of a particular size and sequence (i.e., only those cells containing the knockout construct in the proper position will generate DNA fragments of the proper size).

After suitable ES cells containing the knockout construct in the proper location have been identified, the cells can be inserted into an embryo. Insertion may be accomplished in a variety of ways known to the skilled artisan, however a preferred method is by microinjection. For microinjection, about 10–30 cells are collected into a micropipet and injected into embryos that are at the proper stage of development to permit integration of the foreign ES cell containing the knockout construct into the developing embryo. For instance, as the appended Examples describe, the transformed ES cells can be microinjected into blastocytes.

The suitable stage of development for the embryo used for insertion of ES cells is very species dependent, however for mice it is about 3.5 days. The embryos are obtained by perfusing the uterus of pregnant females. Suitable methods for accomplishing this are known to the skilled artisan, and are set forth by, e.g., Bradley et al. (supra).

While any embryo of the right stage of development is suitable for use, preferred embryos are male. In mice, the preferred embryoGs also have genes coding for a coat color that is different from the coat color encoded by the ES cell genes. In this way, the offspring can be screened easily for the presence of the knockout construct by looking for mosaic coat color (indicating that the ES cell was incorporated into the developing embryo). Thus, for example, if the ES cell line carries the genes for white fur, the embryo selected will carry genes for black or brown fur.

After the ES cell has been introduced into the embryo, the embryo may be implanted into the uterus of a pseudopregnant foster mother for gestation. While any foster mother may be used, the foster mother is typically selected for her ability to breed and reproduce well, and for her ability to care for the young. Such foster mothers are typically prepared by mating with vasectomized males of the same species. The stage of the pseudopregnant foster mother is important for successful implantation, and it is species dependent. For mice, this stage is about 2–3 days pseudopregnant.

Offspring that are born to the foster mother may be screened initially for mosaic coat color where the coat color selection strategy (as described above, and in the appended examples) has been employed. In addition, or as an alternative, DNA from tail tissue of the offspring may be screened for the presence of the knockout construct using Southern blots and/or PCR as described above. Offspring that appear to be mosaics may then be crossed to each other, if they are believed to carry the knockout construct in their germ line, in order to generate homozygous knockout animals. Homozygotes may be identified by Southern blotting of equivalent amounts of genomic DNA from mice that are the product of this cross, as well as mice that are known heterozygotes and wild type mice. Other means of identifying and characterizing the knockout offspring are available. For example, Northern blots can be used to probe the mRNA for the presence or absence of transcripts encoding either the gene knocked out, the marker gene, or both. In addition, Western blots can be used to assess the level of expression of the gene knocked out in various tissues of the offspring by probing the Western blot with an antibody against the particular protein, or an antibody against the marker gene product, where this gene is expressed. Finally, in situ analysis (such as fixing the cells and labeling with antibody) and/or FACS (fluorescence activated cell sorting) analysis of various cells from the offspring can be conducted using suitable antibodies to look for the presence or absence of the knockout construct gene product.

Yet other methods of making knock-out or disruption transgenic animals are also generally known. See, for example, Manipulating the Mouse Embryo, (Cold Spring Harbor Laboratory Press, Cold Spring Harbor, N.Y., 1986). Recombinase dependent knockouts can also be generated, e.g. by homologous recombination to insert target sequences, such that tissue specific and/or temporal control of inactivation of a gene can be controlled by recombinase sequences (described infra).

Animals containing more than one knockout construct and/or more than one transgene expression construct are prepared in any of several ways. The preferred manner of preparation is to generate a series of mammals, each containing one of the desired transgenic phenotypes. Such animals are bred together through a series of crosses, backcrosses and selections, to ultimately generate a single animal containing all desired knockout constructs and/or expression constructs, where the animal is otherwise congenic (genetically identical) to the wild type except for the presence of the knockout construct(s) and/or transgene(s).

4.5 Methods of Treating Diseases

There are a number of diseases or conditions that can be caused by or contributed to by aberrant SR-BI activity in a subject. For example, aberrant SR-BI promoter activity can result in inappropriate lipid transport or metabolism in a subject. For example, individuals who have too low a level of serum HDL cholesterol or too high a level of serum LDL cholesterol are at an increased risk for developing atherosclerosis. Based on the ability of SR-BI receptors to regulate serum cholesterol (e.g., by mediating uptake into tissues), regulating the availability of cellular SR-BI receptors provides useful therapies for atherosclerosis. For instance, molecules described herein, which modulate (e.g. agonize or antagonize) SR-BI promoter activity can be administered to regulate the availability of cellular SR-BI receptors in a subject and thereby provide prophylactic and therapeutic benefit against atherosclerosis.

In addition, the therapeutics of the present invention should prove useful for treating or preventing biliary disorders such as gallstone formation. Since gallstones are known to be caused or contributed to by conditions or factors that increase the ratio of cholesterol to bile acids and lecithin and HDL transports cholesterol from extrahepatic tissue to the liver (e.g. for incorporation into bile).

According to the methods of the invention, a subject having a disease associated with an aberrant SR-BI activity is treated by administration to the subject of an effective amount of a compound which modulates SR-BI activity. A preferred compound is a compound which modulates SR-BI promoter activity. The compound can also be an antagonist of SR-BI promoter activity. Thus, a patient having low SR-BI activity can be treated with an agent which increases SR-BI promoter activity, i.e., an SR-BI promoter agonist. Alternatively, a patient having abnormally high SR-BI promoter activity can be treated with a compound which decreases SR-BI promoter activity, i.e., an SR-BI promoter antagonist.

The compound can be a compound which modulates the interaction of at least one transcription factor with an SR-BI promoter or regulatory element thereof. For example, the compound can inhibit interaction of one of the transcription factors listed in Table I with an SR-BI promoter or regulatory element thereof.

The compound can also be a compound which modulates the activity of a transcription factor binding to an SR-BI promoter or regulatory element thereof. In fact, it is known that the activity of transcription factors can be modulated by post translational modification, e.g., phosphorylation. Accordingly, in one embodiment of the invention, a subject having a condition associated with an aberrant SR-BI activity is treated by administration of a compound which modulates the activity of a transcription factor binding specifically to an SR-BI promoter or regulatory element thereof.

The compound of the invention can also be a compound that modulates the interaction of one transcription factor with another transcription factor. In fact, certain transcription factors are active only if associated with another transcription factor. Alternatively, a transcription factor can be rendered inactive by interaction with another transcription factor.

The compound is preferably selected from the group consisting of nucleic acids, peptides and small molecules. For example, the compound can be an antisense nucleic acid that binds specifically to a region of an SR-BI promoter or regulatory element thereof thereby inhibiting or decreasing promoter activity. The compound can also be an antisense nucleic acid that specifically interacts with a gene encoding a transcription factor modulating SR-BI promoter activity, such that interaction of the antisense nucleic acid with the gene encoding the SR-BI transcription factor will decrease production of this transcription factor, resulting in either an increase or a decrease of SR-BI promoter activity depending on whether the transcription factor enhances or reduces SR-BI promoter activity.

4.5.1. Effective Dose

Toxicity and therapeutic efficacy of such compounds can be determined by standard pharmaceutical procedures in cell cultures or experimental animals, e.g., for determining the $LD_{50}$ (the dose lethal to 50% of the population) and the $ED_{50}$ (the dose therapeutically effective in 50% of the population). The dose ratio between toxic and therapeutic effects is the therapeutic index and it can be expressed as the ratio $LD_{50}/ED_{50}$. Compounds which exhibit large therapeutic indices are preferred. While compounds that exhibit toxic side effects may be used, care should be taken to design a delivery system that targets such compounds to the site of affected tissue in order to minimize potential damage to uninfected cells and, thereby, reduce side effects.

The data obtained from the cell culture assays and animal studies can be used in formulating a range of dosage for use in humans. The dosage of such compounds lies preferably within a range of circulating concentrations that include the $ED_{50}$ with little or no toxicity. The dosage may vary within this range depending upon the dosage form employed and the route of administration utilized. For any compound used in the method of the invention, the therapeutically effective dose can be estimated initially from cell culture assays. A dose may be formulated in animal models to achieve a circulating plasma concentration range that includes the $IC_{50}$ (i.e., the concentration of the test compound which achieves a half-maximal inhibition of symptoms) as determined in cell culture. Such information can be used to more accurately determine useful doses in humans. Levels in plasma may be measured, for example, by high performance liquid chromatography.

4.5.2. Formulation and Use

Pharmaceutical compositions for use in accordance with the present invention may be formulated in conventional manner using one or more physiologically acceptable carriers or excipients. Thus, the compounds and their physiologically acceptable salts and solvates may be formulated for administration by, for example, injection, inhalation or insufflation (either through the mouth or the nose) or oral, buccal, parenteral or rectal administration.

For such therapy, the oligomers of the invention can be formulated for a variety of loads of administration, including systemic and topical or localized administration. Techniques and formulations generally may be found in *Remmington's Pharmaceutical Sciences*, Meade Publishing Co., Easton, Pa. For systemic administration, injection is preferred, including intramuscular, intravenous, intraperitoneal, and subcutaneous. For injection, the oligomers of the invention can be formulated in liquid solutions, preferably in physiologically compatible buffers such as Hank's solution or Ringer's solution. In addition, the oligomers may be formulated in solid form and redissolved or suspended immediately prior to use. Lyophilized forms are also included.

For oral administration, the pharmaceutical compositions may take the form of, for example, tablets or capsules prepared by conventional means with pharmaceutically acceptable excipients such as binding agents (e.g., pregelatinised maize starch, polyvinylpyrrolidone or hydroxypropyl methylcellulose); fillers (e.g., lactose, microcrystalline cellulose or calcium hydrogen phosphate); lubricants (e.g., magnesium stearate, talc or silica); disintegrants (e.g., potato starch or sodium starch glycolate); or wetting agents (e.g., sodium lauryl sulphate). The tablets may be coated by methods well known in the art. Liquid preparations for oral administration may take the form of, for example, solutions, syrups or suspensions, or they may be presented as a dry product for constitution with water or other suitable vehicle before use. Such liquid preparations may be prepared by conventional means with pharmaceutically acceptable additives such as suspending agents (e.g., sorbitol syrup, cellulose derivatives or hydrogenated edible fats); emulsifying agents (e.g., lecithin or acacia); non-aqueous vehicles (e.g., almond oil, oily esters, ethyl alcohol or fractionated vegetable oils); and preservatives (e.g., methyl or propyl-p-hydroxybenzoates or sorbic acid). The preparations may also contain buffer salts, flavoring, coloring and sweetening agents as appropriate.

Preparations for oral administration may be suitably formulated to give controlled release of the active compound.

For buccal administration the compositions may take the form of tablets or lozenges formulated in conventional manner.

For administration by inhalation, the compounds for use according to the present invention are conveniently delivered in the form of an aerosol spray presentation from pressurized packs or a nebuliser, with the use of a suitable propellant, e.g., dichlorodifluoromethane, trichlorofluoromethane, dichlorotetrafluoroethane, carbon dioxide or other suitable gas. In the case of a pressurized aerosol the dosage unit may be determined by providing a valve to deliver a metered amount. Capsules and cartridges of e.g. gelatin for use in an inhaler or insufflator may be formulated containing a powder mix of the compound and a suitable powder base such as lactose or starch.

The compounds may be formulated for parenteral administration by injection, e.g., by bolus injection or continuous infusion. Formulations for injection may be presented in unit dosage form, e.g., in ampoules or in multi-dose containers, with an added preservative. The compositions may take such forms as suspensions, solutions or emulsions in oily or aqueous vehicles, and may contain formulatory agents such as suspending, stabilizing and/or dispersing agents. Alternatively, the active ingredient may be in powder form for constitution with a suitable vehicle, e.g., sterile pyrogen-free water, before use.

The compounds may also be formulated in rectal compositions such as suppositories or retention enemas, e.g., containing conventional suppository bases such as cocoa butter or other glycerides.

In addition to the formulations described previously, the compounds may also be formulated as a depot preparation. Such long acting formulations may be administered by implantation (for example subcutaneously or intramuscularly) or by intramuscular injection. Thus, for example, the compounds may be formulated with suitable polymeric or hydrophobic materials (for example as an emulsion in an acceptable oil) or ion exchange resins, or as sparingly soluble derivatives, for example, as a sparingly soluble salt.

Systemic administration can also be by transmucosal or transdermal means. For transmucosal or transdermal administration, penetrants appropriate to the barrier to be permeated are used in the formulation. Such penetrants are generally known in the art, and include, for example, for transmucosal administration bile salts and fusidic acid derivatives. In addition, detergents may be used to facilitate permeation. Transmucosal administration may be through nasal sprays or using suppositories. For topical administration, the oligomers of the invention are formulated into ointments, salves, gels, or creams as generally known in the art.

In clinical settings, the gene delivery systems for the therapeutic genes can be introduced into a patient by any of a number of methods, each of which is familiar in the art. For instance, a pharmaceutical preparation of the gene delivery system can be introduced systemically, e.g. by intravenous injection, and specific transduction of the protein in the target cells occurs predominantly from specificity of transfection provided by the gene delivery vehicle, cell-type or tissue-type expression due to the transcriptional regulatory sequences controlling expression of the receptor gene, or a combination thereof. In other embodiments, initial delivery of the recombinant gene is more limited with introduction into the animal being quite localized. For example, the gene delivery vehicle can be introduced by catheter (see U.S. Pat. No. 5,328,470) or by stereotactic injection (e.g. Chen et al. (1994) *PNAS* 91: 3054–3057). A promoter, such as the promoter set forth in SEQ ID NO:1, or a sequence homologous thereto can be delivered in a gene therapy construct by electroporation using techniques described, for example, by Dev et al. ((1994) *Cancer Treat Rev* 20:105–115).

The pharmaceutical preparation of the gene therapy construct can consist essentially of the gene delivery system in an acceptable diluent, or can comprise a slow release matrix in which the gene delivery vehicle is imbedded. Alternatively, where the complete gene delivery system can be produced intact from recombinant cells, e.g. retroviral vectors, the pharmaceutical preparation can comprise one or more cells which produce the gene delivery system.

The compositions may, if desired, be presented in a pack or dispenser device which may contain one or more unit dosage forms containing the active ingredient. The pack may for example comprise metal or plastic foil, such as a blister pack. The pack or dispenser device may be accompanied by instructions for administration.

4.6 Diagnostic and Prognostic Assays

The present invention also provides methods for determining if a subject is at risk for the development of a disease or condition that is caused or contributed to by an aberrant SR-BI activity, e.g., an inappropriate lipid transfer or metabolism (e.g., atherosclerosis or a biliary disorder, such as gallstone formation).

In preferred embodiments, the methods of the invention can be characterized as comprising detecting, in a sample of cells from the subject, the presence or absence of a genetic lesion characterized by the mis-expression of a gene whose expression is initiated by an SR-BI promoter. To illustrate, such genetic lesions can be detected by ascertaining the existence of at least one of (i) a deletion of one or more nucleotides from an SR-BI promoter, (ii) an addition of one or more nucleotides to an SR-BI promoter, or (iii) a substitution of one or more nucleotides in an SR-BI promoter. The genetic lesion can also be a chromosomal rearrangement, such as chromosomal dislocation. As set out below, the present invention provides a large number of assay techniques for detecting lesions in an SR-BI promoter or regulatory element thereof.

In one embodiment of the invention, a genetic lesion is identified by a method comprising sequencing a 5'flanking region of an SR-BI gene. Sequencing primers can be designed which hybridize to a portion of an SR-BI 5' flanking region. Primers can also be designed to hybridize to a portion of an SR-BI gene that is transcribed, since this will allow sequencing of the most proximal portion of the promoter. The sequence of the translated portion of the human SR-BI gene, which can be used to design a sequencing primer, can be found, e.g., in Calvo and Vega (1993) *J. Biol. Chemistry* 268:18929. In one embodiment, sequencing primers are located about 250, or about 300 nucleotides apart for sequencing a stretch of about 250 or 300 nucleotides. Examples of primers that can be used include:

—downstream sequencing primer:

5' GGAGACGGGGACGGC 3' (corresponding to nucleotides 5–19 of the human SR-BI cDNA sequence shown in Calvo and Vega, supra) (SEQ ID NO: 8;

—upstream sequencing primer:

5' CTTGTCTTGGCGGCC 3' (corresponding to nucleotides 1401–1415 of SEQ ID NO: 1).

In an exemplary embodiment, there is provided a nucleic acid composition comprising a (purified) oligonucleotide probe or primer including a region of nucleotide sequence which is capable of hybridizing to a sense or antisense sequence of an SR-BI promoter, such as represented in SEQ ID Nos: 1, 2 or 3 or naturally occurring mutants thereof. The nucleic acid of a cell is rendered accessible for hybridization, the probe is exposed to nucleic acid of the sample, and the hybridization of the probe to the sample nucleic acid is detected. It is anticipated that use of an amplification step (e.g. PCR and/or LCR) may be a desirable first step in conjunction with any of the techniques used for detecting mutations described herein.

Alternative amplification methods include: self sustained sequence replication (Guatelli, J. C. et al., 1990, Proc. Natl. Acad. Sci. USA 87:1874–1878), transcriptional amplification system (Kwoh, D. Y. et al., 1989, Proc. Natl. Acad. Sci. USA 86:1173–1177), Q-Beta Replicase (Lizardi, P. M. et al., 1988, Bio/Technology 6:1197), or any other nucleic acid amplification method, followed by the detection of the amplified molecules using techniques well known to those of skill in the art. These detection schemes are especially useful for the detection of nucleic acid molecules if such molecules are present in very low numbers.

In yet another embodiment, any of a variety of sequencing reactions known in the art can be used to directly sequence the SR-BI promoter and detect mutations by comparing the sequence of the sample sequence with the corresponding wild-type (control) sequence. Exemplary sequencing reactions include those based on techniques developed by Maxim and Gilbert (*Proc. Natl Acad Sci USA* (1977) 74:560) or Sanger (Sanger et al (1977) *Proc. Nat. Acad. Sci* 74:5463). It is also contemplated that any of a variety of automated sequencing procedures may be utilized when performing the subject assays (*Biotechniques* (1995) 19:448), including by sequencing by mass spectrometry (see, for example PCT publication WO 94/16101; Cohen et al. (1996) *Adv Chromatogr* 36:127–162; and Griffin et al. (1993) *Appl Biochem Biotechnol* 38:147–159). It will be evident to one skilled in the art that, for certain embodiments, the occurrence of only one, two or three of the nucleic acid bases need be determined in the sequencing reaction. For instance, A-tract or the like, e.g., where only one nucleic acid is detected, can be carried out.

In a further embodiment, protection from cleavage agents (such as a nuclease, hydroxylamine or osmium tetroxide and with piperidine) can be used to detect mismatched bases in RNA/RNA DNA/DNA, or RNA/DNA heteroduplexes (Myers, et al. (1985) *Science* 230:1242). In general, the technique of "mismatch cleavage" starts by providing heteroduplexes of formed by hybridizing (labelled) RNA or DNA containing the wild-type promoter sequence with potentially mutant RNA or DNA obtained from a tissue sample. The double-stranded duplexes are treated with an agent which cleaves single-stranded regions of the duplex such as which will exist due to basepair mismatches between the control and sample strands. For instance, RNA/DNA duplexes can be treated with RNase and DNA/DNA hybrids treated with S1 nuclease to enzymatically digest the mismatched regions. In other embodiments, either DNA/DNA or RNA/DNA duplexes can be treated with hydroxylamine or osmium tetroxide and with piperidine in order to digest mismatched regions. After digestion of the mismatched regions, the resulting material is then separated by size on denaturing polyacrylamide gels to determine the site of mutation. See, for example, Cotton et al (1988) *Proc. Natl Acad Sci USA* 85:4397; Saleeba et al (1992) Methods Enzymod. 217:286–295. In a preferred embodiment, the control DNA or RNA can be labeled for detection.

In other embodiments, alterations in electrophoretic mobility is used to identify mutations in SR-BI promoters. For example, single strand conformation polymorphism (SSCP) may be used to detect differences in electrophoretic mobility between mutant and wild type nucleic acids (Orita et al. (1989) *Proc Natl Acad. Sci USA* 86:2766, see also Cotton (1993) *Mutat Res* 285:125–144; and Hayashi (1992) *Genet Anal Tech Appl* 9:73–79). Single-stranded DNA fragments of sample and control nucleic acids are denatured and allowed to renature. The secondary structure of single-stranded nucleic acids varies according to sequence, the resulting alteration in electrophoretic mobility enables the detection of even a single base change. The DNA fragments may be labelled or detected with labelled probes. The sensitivity of the assay may be enhanced by using RNA (rather than DNA), in which the secondary structure is more sensitive to a change in sequence. In a preferred embodiment, the subject method utilizes heteroduplex analysis to separate double stranded heteroduplex molecules on the basis of changes in electrophoretic mobility (Keen et al. (1991) Trends Genet 7:5).

In yet another embodiment the movement of mutant or wild-type fragments in polyacrylamide gels containing a gradient of denaturant is assayed using denaturing gradient gel electrophoresis (DGGE) (Myers et al (1985) Nature 313:495). When DGGE is used as the method of analysis, DNA will be modified to insure that it does not completely denature, for example by adding a GC clamp of approximately 40 bp of high-melting GC-rich DNA by PCR. In a further embodiment, a temperature gradient is used in place of a denaturing agent gradient to identify differences in the mobility of control and sample DNA (Rosenbaum and Reissner (1987) Biophys Chem 265:1275).

Examples of other techniques for detecting point mutations include, but are not limited to, selective oligonucleotide hybridization, selective amplification, or selective primer extension. For example, oligonucleotide primers may be prepared in which the known mutation is placed centrally and then hybridized to target DNA under conditions which permit hybridization only if a perfect match is found (Saiki et al. (1986) *Nature* 324:163); Saiki et al (1989) *Proc. Natl Acad. Sci USA* 86:6230). Such allele specific oligonucleotide hybridization techniques may be used to test one mutation per reaction when oligonucleotides are hybridized to PCR amplified target DNA or a number of different mutations when the oligonucleotides are attached to the hybridizing membrane and hybridized with labeled target DNA.

Alternatively, allele specific amplification technology which depends on selective PCR amplification may be used in conjunction with the instant invention. Oligonucleotides used as primers for specific amplification may carry the mutation of interest in the center of the molecule (so that amplification depends on differential hybridization) (Gibbs et at (1989) *Nucleic Acids Res.* 17:2437–2448) or at the extreme 3' end of one primer where, under appropriate conditions, mismatch can prevent, or reduce polymerase extension (Prossner (1993) *Tibtech* 11:238. In addition it may be desirable to introduce a novel restriction site in the region of the mutation to create cleavage-based detection (Gasparini et al (1992) *Mol. Cell Probes* 6:1). It is anticipated that in certain embodiments amplification may also be performed using Taq ligase for amplification (Barany (1991) *Proc. Natl. Acad. Sci USA* 88:189). In such cases, ligation will occur only if there is a perfect match at the 3' end of the 5' sequence making it possible to detect the presence of a known mutation at a specific site by looking for the presence or absence of amplification.

In another embodiment, the invention provides a method for determining whether a subject is at risk of developing a disease or condition which is caused by or contributed by an aberrant SR-BI promoter activity, comprising detecting the level of SR-BI mRNA or protein in a subject and comparing that level to a normal standard, wherein a level lower than the standard level indicates that the subject has or is at risk for developing a disease or condition which is caused by or contributed by an aberrant SR-BI promoter activity. SR-BI mRNA levels can be determined by isolating cells of a subject and measuring the amount of mRNA, by using Northern blot hybridization, in situ hybridizations, or methods based on PCR. Protein levels can be determined by immunohistochemisty or immunoprecipitation.

Another embodiment of the invention provides for a nucleic acid composition comprising a (purified) oligonucleotide probe including a region of nucleotide sequence which is capable of hybridizing to a sense or antisense sequence of an SR-BI promoter, or naturally occurring mutants thereof, or 5' or 3' flanking sequences. The nucleic acid of a cell is rendered accessible for hybridization, the probe is exposed to nucleic acid of the sample, and the hybridization of the probe to the sample nucleic acid is detected. Such techniques can be used to detect lesions at either the genomic or mRNA level, including deletions, substitutions, etc., as well as to determine mRNA transcript levels. Such oligonucleotide probes can be used for both predictive and therapeutic evaluation of allelic mutations which might be manifest in, for example, neoplastic or hyperplastic disorders (e.g., aberrant cell growth).

The methods described herein may be performed, for example, by utilizing pre-packaged diagnostic kits comprising at least one probe nucleic acid or antibody reagent described herein, which may be conveniently used, e.g., in clinical settings to diagnose patients exhibiting symptoms or family history of a disease or illness involving aberrant lipid transfer or metabolism.

Any cell type or tissue may be utilized in the diagnostics described below. For example, a subject's bodily fluid (e.g. blood) can be obtained by known techniques (e.g. venipuncture). Alternatively, nucleic acid tests can be performed on dry samples (e.g. hair or skin). Fetal nucleic acid samples can be obtained from maternal blood as described in International Patent Application No. WO91/07660 to Bianchi. Alternatively, amniocytes or chorionic villi may be obtained for performing prenatal testing.

Diagnostic procedures may also be performed in situ directly upon tissue sections (fixed and/or frozen) of patient tissue obtained from biopsies or resections, such that no nucleic acid purification is necessary. Nucleic acid reagents may be used as probes and/or primers for such in situ procedures (see, for example, Nuovo, G. J., 1992, PCR in situ hybridization: protocols and applications, Raven Press, NY).

In addition to methods which focus primarily on the detection of one nucleic acid sequence, profiles may also be assessed in such detection schemes. Fingerprint profiles may be generated, for example, by utilizing a differential display procedure, Northern analysis and/or RT-PCR.

Moreover, it will be understood that any of the above methods for detecting alterations in an SR-BI promoter can be used to monitor the course of treatment or therapy.

The present invention is further illustrated by the following examples which should not be construed as limiting in any way. The contents of all cited references (including literature references, issued patents, published patent applications as cited throughout this application are hereby expressly incorporated by reference. The practice of the present invention will employ, unless otherwise indicated, conventional techniques of cell biology, cell culture, molecular biology, transgenic biology, microbiology, recombinant DNA, and immunology, which are within the skill of the art. Such techniques are explained fully in the literature. See, for example, *Molecular Cloning A Laboratory Manual,* 2nd Ed., ed. by Sambrook, Fritsch and Maniatis (Cold Spring Harbor Laboratory Press: 1989); *DNA Cloning,* Volumes I and II (D. N. Glover ed., 1985); *Oligonucleotide Synthesis* (M. J. Gait ed., 1984); Mullis et al. U.S. Pat. No: 4,683,195; *Nucleic Acid Hybridization* (B. D. Hames & S. J. Higgins eds. 1984); Transcription And Translation (B. D. Hames & S. J. Higgins eds. 1984); *Culture Of Animal Cells* (R. I. Freshney, Alan R. Liss, Inc., 1987); *Immobilized Cells And Enzymes* (IRL Press, 1986); B. Perbal, *A Practical Guide To Molecular Cloning* (1984); the treatise, *Methods In Enzymology* (Academic Press, Inc., N.Y.); *Gene Transfer Vectors For Mammalian Cells* (J. H. Miller and M. P. Calos eds., 1987, Cold Spring Harbor Laboratory); *Methods In Enzymology,* Vols. 154 and 155 (Wu et al. eds.), *Immunochemical Methods In Cell And Molecular Biology* (Mayer and Walker, eds., Academic Press, London, 1987); *Hand-* book Of Experimental Immunology, Volumes I–IV (D. M. Weir and C. C. Blackwell, eds., 1986); Manipulating the Mouse Embryo, (Cold Spring Harbor Laboratory Press, Cold Spring Harbor, N.Y., 1986).

5. EXAMPLES

The invention now being generally described, it will be more readily understood by reference to the following examples which are included merely for purposes of illustration of certain aspects and embodiments of the present invention, and are not intended to limit the invention.

5.1 Identification and Characterization of the Human SR-BI Promoter

A BAC clone containing the gene for SR-BI was obtained from Research Genetics (Huntsville, Ala.). From this BAC, a sheared library was constructed and then sequenced. A region upstream of the exon containing the start ATG was identified by using GRAIL to be a likely promoter region. This region was isolated by BamHI digestion from a clone in the BAC library resulting in the 1.6 kb fragment, termed herein sa-12, having the nucleotide sequence shown in FIG. 1 (SEQ. ID. NO: 1).

The 1.6 kb nucleic acid sa-12 was then inserted into a reporter construct, pGL3-basic (pGL3-b) (Promega, Madison, Wis.), which was transfected into hepatocellular carcinoma cells, HepG2 cells, which were then analyzed for luciferase activity and compared with expression from pGL3-b vector containing either the cytomegalovirus (CMV) promoter, the ApoAI promoter, or no promoter.

The luciferase assay was performed as follows. The transfected cells were washed with phosphate buffered saline (PBS) and lysed with 500 µl of lysis buffer (50 mM Tris, 150 mM NaCl, 0.02% NaAzide, 1% NP-40, 100 µg/ml AEBSF, and 5 µg/ml Leupeptin). 50 µl of this lysate was added to 100 µl luciferase substrate (Promega) and read in a microβ-plate reader within 5 minutes of adding the lysate. Data are expressed as units of relative luciferase activity. Reporter constructs producing high levels of luciferase in transfected cells are those which contain an SR-BI promoter fragment capable of stimulating transcription.

FIG. 2 shows luciferase activity by the CMV promoter (which works well in virtually all cells), the liver specific ApoA1 promoter and the SR-BI promoter. While there was essentially no expression from the promoterless pGL3-b construct, expression was evidenced for the CMV, ApoA1 and SR-BI promoters. These results show that the 1.6 kb sa-12 nucleic acid includes a promoter that is capable of initiating gene transcription in hepatic cells.

Figure 3:
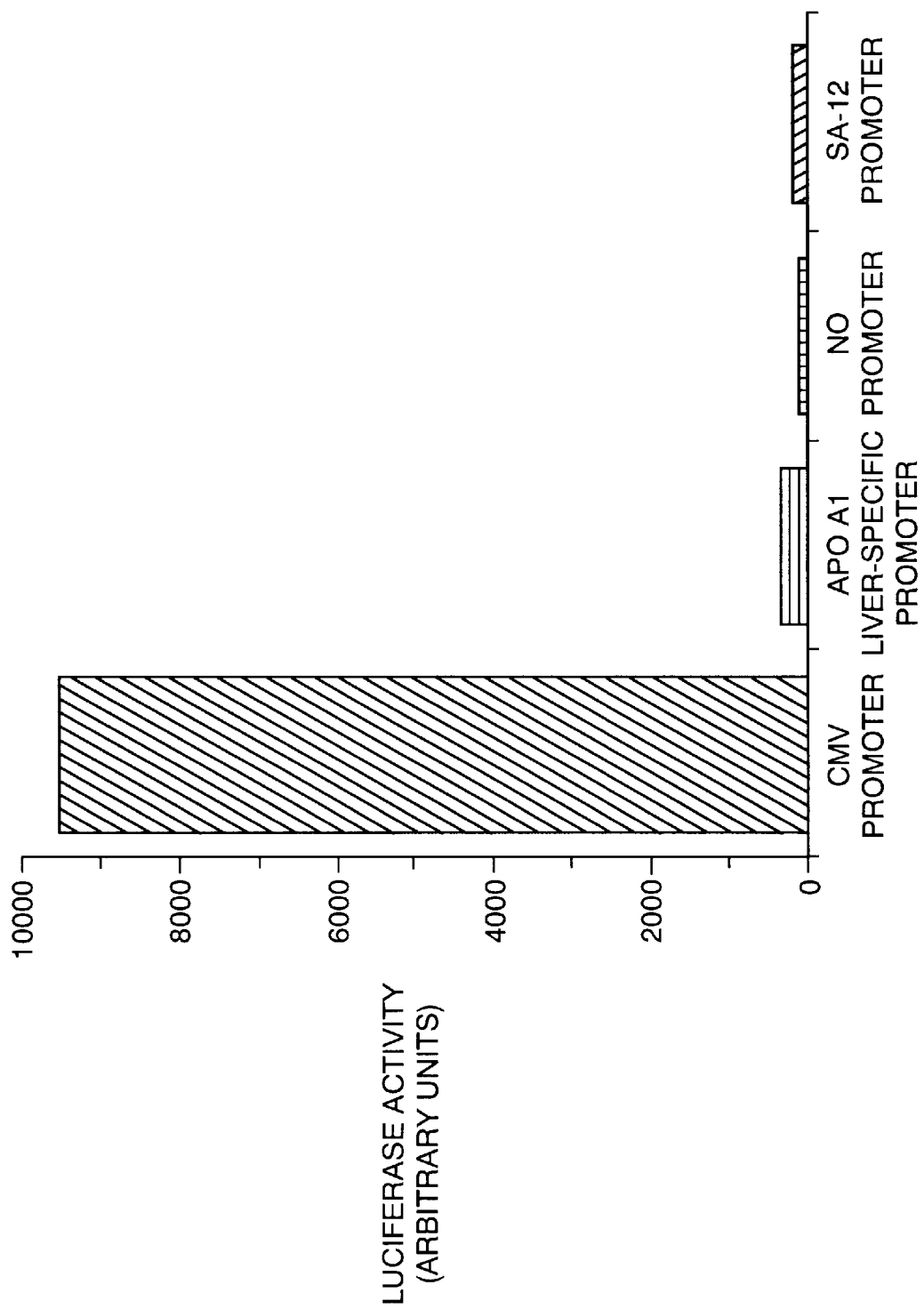
FIG. 3 is a bar graph plotting luciferase activity from ECV endothelial cells, which were transiently transfected with the pGL3-Basic promoterless vector alone or driven by: the cytomegalovirus (CMV) promoter, the ApoA1 liver specific promoter, or the SR-BI promoter (sa-12).

FIG. 3 shows the luciferase activity from ECV endothelial cells, which were transiently transfected with the pGL3-b promoterless vector alone or driven by the CMV promoter, the ApoA1 liver specific promoter, or the SR-BI nucleic acid sa-12. As expected, the liver specific promoter of the ApoI gene was not active in ECV cells relative to the CMV control. However, in addition, the SR-BI nucleic acid sa-12 was not active in these cells, suggesting that the SR-BI promoter has cell-specific properties (i.e., is functional in hepatocytes, but not in endothelial cells).

5.2 Northern Analysis of Human SR-BI mRNA

This example describes a Northern blot analysis of the expression of SR-BI in various tissues.

The probes were prepared using the Multiprime Labeling Kit (Amersham Life Sciences, Cleveland Ohio), essentially by combining 4 ml of an ApaI 286bp fragment of SR-BI cDNA, 10 ml multiprime buffer solution, 5 ml primer solution, 24 ml $H_2O$, 5 ml $^{32}PdCTP$ and 2 ml Klenow fragment. The mixture was incubated at 37° for 30 minutes. The probe was then purified using a Biospin 6 column (Biorad; Hercules, Calif.).

Clontech Multiple Tissue Northern (MTN) blots (LaJolla, Calif.) were hybridized overnight at 65° C. in 1×nylon wash and $1\times10^6$ cpm/ml of probe, which was denatured in ice prior to addition to the hybridization buffer. Blots were washed in 0.5× nylon wash (14% SDS, 130 mM $Na_2 HPO_4$, 14 mM $Na_4$ EDTA, and 0.2% Triton X100) three times for 30 minutes at 65° C.

The results of this hybridization indicate that the 286 bp SR-BI probe hybridizes to a major 2.9 kb band and to minor bands of much higher molecular weight in most tissues. The mRNA was found to be most highly expressed in adrenals, ovaries, and liver, thus indicating that SR-BI is expressed in these tissues. Interestingly, SR-BI was also found to be expressed at high levels in placenta. Thus, the SR-BI promoter is active in these tissues, further indicating the tissue specificity of this promoter.

5.3 Assays for Identifying SR-BI Promoter Fragments and Regulatory Elements Capable of Reglulating Transcription of a Gene to Which it is Operably Linked This example describes assays for identifying regions in the 5' flanking portion of the SR-BI gene which are capable of regulating expression of a gene to which such a portion is operably linked.

In one assay, various fragments of the SR-BI nucleic acid shown in FIG. 1 (SEQ ID NO: 1) or present in nucleic acid having ATCC Deposit No. 98304 are cloned upstream of the luciferase gene in the multiple cloning site of the pGL3-b vector (Promega). The nucleic acid fragments can be fragments having the 3' end of the promoter region and extending to various positions upstream of the transcription initiation site. The nucleic acid fragments can also be chosen based on the potential transcription factor binding sites identified in the TF Search described above. Accordingly, nucleic acid fragments containing one or more of these potential binding sites are prepared, e.g., by polymerase chain reaction (PCR), and cloned in pGL3-b vector. To prepare positive controls for this assay, promoters of CMV, liver-specific ApoA1 are also inserted in pGL3-b.

The vectors are then transiently transfected in cells expressing SR-BI, such as HepG2 cells. For the transfection, HepG2 cells are plated onto poly-D-lysine coated 6-well dishes and allowed to attach overnight. The cells are transfected with the prepared reporter constructs using lipofectamine following the manufacturer's instructions (Gibco). Forty-eight hours following the transfection, the cells are assayed for luciferase activity as described in Example 5.1.

In another example, regulatory elements of the 5' flanking region of the SR-BI gene are identified. Fragments of the SR-BI nucleic acid shown in FIG. 1 (SEQ ID NO: 1 can then be inserted upstream of a basic promoter in a reporter construct containing the luciferase gene, such as the pGLZ promoter vector from Promega. This will permit the identification of SR-BI promoter fragments which act as enhancers or silencers of a basic promoter. In this assay, the same or different promoter fragments as those described above are cloned in the reporter vector containing a basic promoter. Hep-G2 cells or other SR-BI positive cells are transiently transfected with the reporter constructs and the level of expression of luciferase is measured as described above. Accordingly, reporter constructs containing SR-BI promoter fragments resulting in higher expression of the luciferase gene compared to the reporter construct containing only the basic promoter contain an SR-BI enhancer element. Reporter constructs containing SR-BI promoter fragments resulting in lower expression of the luciferase gene compared to the reporter construct containing only the basic promoter contain an SR-BI silencer element.

In yet another example, a method is used that allows the screening of a high number of promoter fragments for transcription modulating activity. In this method, the SR-BI promoter shown in FIG. 1 is subjected to digestion with an exonuclease, e.g., BalI, and aliquots of the digestion are removed at various time points to generate promoter fragments of various sizes. These mixtures of promoter fragments are then cloned upstream of a reporter gene encoding a selection marker, e.g, a protein providing resistance to a drug. Hep-G2 cells are stably transfected with the mixtures of reporter constructs and cultured in medium containing the drug to which the selection marker provides resistance. Thus, clones of stably transfected cells containing an SR-BI promoter fragment which is capable of stimulating transcription of the reporter gene can be isolated. The identity of the promoter fragment is determined by PCR amplification and sequencing.

The assay described in the previous paragraph can also be used to identify enhancer elements present in the promoter. In this particular assay, the reporter construct in which the SR-BI promoter fragments are inserted contains a basic promoter providing low level expression of the reporter gene. Reporter constructs containing an enhancer element will allow high level expression of the selection marker.

A similar assay can be used to identify silencer elements present in the SR-BI promoter. In this particular assay, the reporter construct contains a basic promoter resulting in relatively high transcription of the reporter gene. Furthermore, in this assay, the reporter gene encodes a protein which stimulates cell death. Such genes are known in the art. Thus, only cells containing a reporter construct containing a silencer will survive.

5.4 Tissue Culture Based Reporter Assay for Identifying Compounds Which Modulate SR-BI Promoter Activity In this assay, pGL3-b containing the SR-BI promoter shown in FIG. 1 or a fragment thereof, which has transcriptional activity, and located upstream of the luciferase gene is stably transfected into Hep-G2 cells. These stably transfected cells are then distributed in 96 well plates, incubated overnight, and the test compounds are added to individual wells. Following incubation for an appropriate amount of time, the cells are washed and lysed as described above. The amount of luciferase present in each well is determined using the luciferase assay described above and reading of the optical density with a 96 well plate reader. This technique allows rapid and simultaneous testing of numerous compounds and dosages of these compounds.

5.5 In vivo Assay for Identifying Compounds That Modulate SR-B1 Promoter Activity Once a compound modulating the SR-B 1 promoter activity has been identified, e.g., by using the tissue culture based reporter assay described above, the effect of the compound can be tested in vivo as follows.

The test compound is administered to a non-human mammal, such as a mouse, and the level of expression of SR-BI is measured and compared to its level of expression in an animal to which the compound was not administered. The compound can be administered locally or systemically and various dosages can be tested. At various times after administration of the compound to the animal, the animal is sacrificed and the level of expression of the SR-BI gene is measured in tissues known to express SR-BI, e.g., adrenal glands, ovaries, and liver, and in other tissues. The determination of the level of expression of SR-BI in tissues not known to express SR-BI will indicate whether a test compound is capable of stimulating the expression of the SR-BI gene in tissues which do not normally express the protein.

The level of expression of SR-BI in the tissues can be measured by Northern blot analysis as described above, using a probe hybridizing specifically to the mouse SR-BI mRNA. A cDNA encoding a mouse SR-BI protein is described in Acton et al. (1996) *Science* 271:518. mRNA is isolated from the tissues, as described, e.g., in Sambrook, J. Fritsch, E. F., and Maniatis, T. (1989) *Molecular Cloning: A Laboratory Manual,* Cold Spring Harbor Laboratory Press, Cold Spring Harbor, N.Y. To determine the level of expression of SR-BI in individual cells, one can use in situ hybridization on tissue sections.

Alternatively, the level of expression of SR-BI can be determined by measuring the level of SR-BI protein, such as by immunohistochemistry using an antibody binding specifically to SR-BI. Such an antibody is described, e.g., in Acton et al., supra.

Comparison of the level of expression of SR-BI will indicate whether the test compound modulates transcription from the SR-BI promoter in vivo. Thus, a higher level of SR-BI mRNA and/or protein in the mice to which the test compound was administered as compared to mice to which the compound was not administered indicates that the test compound stimulates the SR-BI promoter in vivo. A lower level of SR-BI mRNA and/or protein in the mice to which the test compound was administered as compared to mice to which the compound was not administered indicates that the test compound inhibits transcription from the SR-BI promoter in vivo.

In another example, the effect of the test compound on the human SR-BI promoter is measured in vivo. Accordingly, a mouse transgenic for a reporter gene which is operably linked to and positioned downstream of the human SR-BI promoter is prepared, according to techniques known in the art and described above. The reporter gene is, for example, a gene encoding beta-galactosidase (LacZ). The transgenic mouse is then treated with the test compound or with nothing, as described above, sacrificed, and the level of expression of the reporter gene is measured in various tissues using, e.g., a colorimetric assay. For example, the level of expression of the beta-galactosidase gene can be determined by performing a beta-galactosidase assay, according to methods known in the art. Comparison of the level of expression of the reporter gene will indicate whether the test compound modulates transcription from the human SR-BI promoter in vivo.

The reporter gene can also be a gene encoding any marker protein which can be recognized, for example, by an antibody or through specific binding to another molecule.

5.6 Assay for Identifying Transcriptional Regulatory Molecule Binding Sites in the SR-BI Promoter This example describes a method for determining the sites of binding of transcription factors in the SR-BI promoter.

Fragments of the SR-BI promoter of about 20 to about 150 base pairs are prepared. Short fragments of up to about 30 base pairs are prepared by synthesis of oligonucleotides and annealing of the two complementary strands. The fragments are chosen, e.g., to contain one or more of the potential transcription factor binding sites identified in the computer based transcription factor binding site search performed. For example, SR-BI promoter fragments containing the Nkx-2, USF, MZF1, SRY, GATA- 1, GATA-2, GATA-3, Sox-5, and/or Lyf-1 binding sites can be prepared. As negative controls, mutated versions of these double stranded oligonucleotides are prepared. Such fragments are then radiolabelled, incubated with or without cell extracts prepared from cells expressing or not expressing SR-BI, and subjected to an electrophoretic mobility shift assay (EMSA), as described, e.g., in Sambrook, J. Fritsch, E. F., and Maniatis, T. (1989) *Molecular Cloning: A Laboratory Manual*, Cold Spring Harbor Laboratory Press, Cold Spring Harbor, N.Y. Cell extracts can be prepared from Hep-G2 cells which express SR-BI and from endothelial cells which do not express SR-BI.

An EMSA assay can be performed as follows. A partially purified or recombinant Transcriptional Regulatory Molecule of an SR-BI promoter or a cell extract are incubated with 25,000 cpm (20 fmol) of $^{32}$P-labeled blunt-ended probe (comprised of an SR-BI promoter that contains the transcriptional regulatory molecule binding site.) in a reaction mixture containing 10% sucrose, 3.75 mM HEPES, pH 7.6, 2.75 mM MgCl$_2$, 1.5 mM spermidine, 200 ng of poly (dI-dC), 100 mg of bovine serum albumin and 75 ng of sonicated salmon sperm DNA at room temperature for at least 30 minutes, then separated by 5% nondenaturing polyacrylamide gel electrophoresis (PAGE) in 0.5 TBE buffer at 100V for at least 2 hours.

Comparison of the binding pattern of SR-BI positive cells to SR-BI negative cells for each SR-BI promoter fragment in these EMSA assays will indicate differences in binding of transcription factors to specific regions of the SR-BI promoter. Accordingly, a difference in binding pattern to a specific region of the promoter will indicate the likely involvement of this region of the promoter in regulation of transcription from the promoter.

5.7 In vitro Assay for Identifying Compounds that Modulate Binding of Transcriptional Regulatory Molecules to an SR-BI Promoter This example describes a method that allows the identification of compounds which modulate binding of transcription factors to the SR-BI promoter and which are thus likely to modulate transcription from the SR-BI promoter.

According to this assay, cell extracts are prepared from cells expressing SR-BI and cells which do not express SR-BI. These cell extracts are then incubated with radiolabeled fragments of the SR-BI promoter, as described in the previous section, in the presence of various concentrations of the test compound. After about 20 minutes of incubation, these mixtures are submitted to EMSA, also as described in the previous section. Comparison of the binding pattern of extracts and promoter fragments incubated with or without the test compound will indicate whether the test compound inhibits binding of one or more transcription factors to the promoter fragment.

This assay can be performed using SR-BI promoter fragments to which proteins bind in cells expressing SR-BI and in cells which do not express SR-BI. In fact, proteins binding to the promoter in both cell types may be proteins required for stimulating transcription or for inhibiting transcription whose effect on the promoter is mediated by modifications of the protein, such as phosphorylation. Alternatively, this assay can be performed using SR-BI promoter fragments to which proteins bind only in cells expressing SR-BI or only in cells which do not express SR-BI.

This assay can be performed in the form of a high throughput assay. For example, proteins of the cell extract are attached to 96 well plates and the DNA binding reactions are carried in the individual wells in the presence or absence of a test compound. After the binding reaction, the wells are washed to removed unbound DNA and the amount of labeled DNA attached to the wells is determined by measuring the amount of label in each well.

5.8 Isolation of Transcription Regulatory Molecules Binding to the SR-BI Promoter This example describes methods for cloning transcription factors binding to the SR-BI promoter.

In one example, transcription factors are isolated using the λgt11 method well known in the art. In this method, λAgt11 expression library is constructed using mRNA from cells which express SR-BI, such as Hep-G2 cells. The expression library is then screened with a probe consisting of a fragment of the SR-BI promoter, shown to be involved in stimulation of transcription and to which proteins have been shown to bind in the assays described above.

In another example, transcription factors binding to the SR-BI promoter are isolated by affinity purification chromatography in which nuclear extracts from cells expressing SR-BI are passed over an affinity column containing the SR-BI promoter or functional fragment thereof. Extracts from the column are tested for the presence of promoter binding factors by EMSA, as described above. Following sufficient purification, the amino acid sequence of the N-terminal portion of the binding factor is determined by sequencing. Based on the amino acid sequence obtained, degenerate oligonucleotides are synthesized and used to screen cDNA libraries prepared from cells expressing SR-BI.

In yet another example, transcription factors binding to the SR-BI promoter are isolated using a yeast 1-hybrid system. In this assay, a cDNA expression library is constructed from mRNA obtained from cells expressing SR-BI. In this expression library, the cDNAs are cloned next to a nucleic acid sequence encoding an activator protein, i.e., a protein which is capable of activating transcription, such that expression of the nucleic acid results in the synthesis of a fusion protein consisting of the protein encoded by the cDNA fused to the activator protein. This expression library is then introduced into yeast cells which have been modified to contain a reporter construct having an SR-BI promoter or regulatory element thereof. These yeast cells are then selected for those expressing the reporter construct, since these will be yeast cells containing a cDNA encoding a protein which binds to the SR-BI promoter and thus allowing the activator protein to stimulate transcription of the reporter construct. Such 1-hybrid yeast systems are well known in the art and are described, e.g, in Li and Herskowitz (1993) *Science* 262:1870 and Wang and Reed (1993) *Nature* 364:121.

Once a factor binding to the SR-BI promoter has been identified, its role in regulating transcription from this promoter can be determined. This can be determined by transient transfection assays in which an expression vector containing the identified factor is cotransfected in cells which do not express SR-BI and/or the factor with a reporter construct containing the SR-BI promoter. Increased expression of the reporter construct as compared to expression of the reporter construct in cells not transfected with the expression construct will indicate that the isolated factor is capable of binding and activating transcription from the SR-BI promoter. Alternatively, a lower level of expression of the reporter gene in cells transfected with the expression construct as compared to cells not transfected with the expression construct will indicate that the identified factor is an inhibitory factor.

The isolation of a nucleic acid encoding a transcription factor regulating the activity of SR-BI promoter will allow modulation of the SR-BI, by increasing the amount of the transcription factor. The amount of transcription factor can be increased by introducing an expression vector encoding the transcription factor into cells according to methods described herein. Alternatively, a recombinant form of the transcription factor can be introduced into the cells.

5.9 Assays for Isolating Compounds Which Inhibit Binding of a Transcription Factor to the SR-BI Promoter Factors binding to the SR-BI promoter can be factors which upon binding stimulate transcription, i.e., activators, or which repress transcription, i.e., inhibitors. Accordingly, inhibition of binding of such transcription factors to the SR-BI promoter will result in inhibition or stimulation of transcription from the promoter. Compounds which inhibit binding of transcription factors to the SR-BI promoter can be identified as follows.

The transcription factor is produced recombinantly, such as in *E. coli* and purified. This protein is then incubated in vitro together with labeled SR-BI promoter, as described above in the EMSA assays, in the presence or absence of the test compound. Following incubation, the mixtures are submitted to EMSA and autoradiography. Reduced amount of retarded complex in binding reactions containing a test compound indicates that the test compound interferes with binding of the factor to the SR-BI promoter.

In another assay, the recombinant transcription factor is attached to 96 well plates and the DNA binding reactions are carried in the individual wells in the presence or absence of a test compound. After the binding reaction, the wells are washed to removed unbound DNA and the amount of labeled DNA attached to the wells is determined by measuring the amount of label in each well. This assay is a rapid and efficient method for testing numerous compounds.

Deposit of Microorganisms

*E. coli* plasmid pSA-12 was deposited with the American Type Culture Collection Rockville, Md., on Jan. 23, 1997 under the terms of the Budapest Treaty and assigned accession number 98304.

All of the above-cited references and publications are hereby incorporated by reference.

Equivalents

Those skilled in the art will recognize, or be able to ascertain using no more than routine experimentation, many equivalents to the specific embodiments of the invention described herein. Such equivalents are intended to be encompassed by the following claims.

What is claimed is:

1. An isolated nucleic acid molecule which is capable of hybridizing to a nucleic acid molecule consisting of the nucleotide sequence from nucleotide 610 to nucleotide 1595 of SEQ ID NO: 1 or the complement thereof in a medium having a salt concentration of about 6.0×sodium chloride/sodium citrate (SSC) and a temperature of about 45° C.

2. An isolated nucleic acid molecule of claim 1, which is capable of hybridizing to a nucleic acid molecule consisting of the nucleotide sequence from nucleotide 610 to nucleotide 1595 of SEQ ID NO: 1 or complement thereof in a medium having a salt concentration of about 2.0×sodium chloride/sodium citrate (SSC) and a temperature of about 45° C.

3. An isolated nucleic acid molecule of claim 1, which further comprises a label.

4. An isolated nucleic acid molecule of claim 1, wherein the nucleic acid is capable of modulating transcription of a gene operably linked to the nucleic acid.

5. An isolated nucleic acid molecule of claim 4, wherein the gene encodes an SR-BI receptor.

6. An isolated nucleic acid molecule of claim 4, wherein the nucleic acid is capable of activating transcription of a gene operably linked to the nucleic acid.

7. An isolated nucleic acid molecule of claim 4, wherein the nucleic acid is capable of enhancing transcription of a gene operably linked to the nucleic acid.

8. An isolated nucleic acid molecule of claim 4, which is operably linked to a gene.

9. A vector comprising a nucleic acid molecule of claim 4.

10. A vector of claim 9, which is capable of replicating in a cell.

11. An isolated host cell comprising a vector of claim 9.

12. An isolated host cell of claim 11, which is a liver cell.

13. A transgenic mouse having integrated into its genome a transgene comprising a nucleic acid of claim 6 operably linked to a coding sequence, and wherein the transgene is expressed in adrenal glands.

14. An isolated nucleic acid of claim 1, that is capable of regulating expression of a selected DNA sequence operably linked thereto.

15. An isolated nucleic acid of claim 14 that is an SR-BI basic promoter.

16. An isolated nucleic acid molecule of claim 14 that is an SR-BI regulatory element.

17. An isolated nucleic acid molecule of claim 14, which is operably linked to a gene.

18. A method for identifying a test compound that modulates transcription from an SR-BI promoter, comprising the steps of:

(i) combining in a cell or cellular extract, the test compound and a reporter construct comprised of a reporter gene, operably linked to an SR-BI promoter comprising the nucleic acid sequence shown in FIG. 1 (SEQ ID NO: 1); and (ii) detecting the level of expression of the reporter gene, wherein a statistically significant change in the level of expression relative to expression in the absence of the test compound indicates that the test compound modulates the activity of an SR-BI promoter.

19. A method for identifying a test compound that modulates transcription from an SR-BI promoter comprising the steps of:

(i) combining in a cell or cellular extract, the test compound and a reporter construct comprised of a reporter gene operably linked to an SR-BI promoter comprising at least about 5 and less than about 40 consecutive nucleotides of the nucleic acid sequence shown in FIG. 1 (SEQ ID NO: 1); and (ii) detecting the level of expression of the reporter gene, wherein a statistically significant change in the level of expression relative to expression in the absence of the test compound indicates that the test compound modulates the activity of an SR-BI promoter.

20. A method of claim 19, wherein the SR-BI promoter comprises at least about 15 and less than about 30 consecutive nucleotides of the nucleic acid sequence shown in FIG. 1 (SEQ ID NO: 1).

21. A method of claim 18, wherein the cell or cellular extract is a hepatic cell or cellular extract from a hepatic cell.

22. A method of claim 18, wherein the reporter construct is comprised of at least one SR-BI regulatory element.

23. A method of claim 18, wherein the compound is selected from the group consisting of a nucleic acid, a peptide, and a small molecule.

24. A method of claim 18, wherein the reporter molecule is a luciferase.

25. An isolated nucleic acid molecule contained in ATCC Deposit No 98304.

26. An isolated nucleic acid comprising a nucleotide sequence set forth in any of SEQ ID NO: 1, 2 or 3 or the complement of a nucleic acid set forth in any of SEQ ID NO: 1, 2, or 3.

27. The isolated nucleic acid of claim 26 comprising the nucleotide sequence set forth in SEQ ID NO: 1 or the complement of SEQ ID NO: 1.

28. An isolated nucleic acid comprising the nucleotide sequence from about nucleotide 610 to about nucleotide 1595 of SEQ ID NO: 1.

29. An isolated nucleic acid comprising the nucleotide sequence from about nucleotide 900 to about nucleotide 1595 of SEQ ID NO: 1.

30. A method for preparing a non-human transgenic mouse, comprising introducing into the mouse a transgene comprising a nucleic acid of claim 6 operably linked to a coding sequence, to thereby obtain a non-human transgenic mouse expressing the transgene in adrenal glands.

31. An isolated nucleic acid of claim 27 consisting of the nucleotide sequence set forth in SEQ ID NO: 1 or the complement of SEQ ID NO: 1.

* * * * *